United States Patent
Kim et al.

(10) Patent No.: US 10,316,013 B2
(45) Date of Patent: Jun. 11, 2019

(54) ORGANIC LIGHT EMITTING COMPOUND AND ORGANIC LIGHT EMITTING DEVICE INCLUDING THE SAME

(71) Applicant: SFC CO., LTD., Cheongju-si (KR)

(72) Inventors: Jeong-Soo Kim, Hongsung-gun (KR); Yeon-kwon Ryu, Cheongwon-gun (KR); Sang-Won Ko, Incheon (KR); Su-Jin Lee, Busan (KR); Ji-Hwan Kim, Anyang-si (KR); Ji-young Kim, Sungjoo-gun (KR)

(73) Assignee: SFC Co., Ltd., Cheongju-si (KR)

( * ) Notice: Subject to any disclaimer, the term of this patent is extended or adjusted under 35 U.S.C. 154(b) by 199 days.

(21) Appl. No.: 14/712,550

(22) Filed: May 14, 2015

(65) Prior Publication Data

US 2015/0333277 A1    Nov. 19, 2015

(30) Foreign Application Priority Data

May 14, 2014  (KR) .................. 10-2014-0057851

(51) Int. Cl.
  *C07D 221/20*  (2006.01)
  *C07D 307/94*  (2006.01)
  (Continued)

(52) U.S. Cl.
  CPC .......... *C07D 311/80* (2013.01); *C07D 221/20* (2013.01); *C07D 307/94* (2013.01);
  (Continued)

(58) Field of Classification Search
  CPC .. C07D 311/80; C07D 335/10; C07D 311/92; C07D 307/94; H01L 51/0094;
  (Continued)

(56) References Cited

U.S. PATENT DOCUMENTS

2003/0168970 A1*  9/2003  Tominaga .............. C07C 15/28
                                                            313/504
2012/0211735 A1†  8/2012  Imada

FOREIGN PATENT DOCUMENTS

KR    20120015883 A    †  2/2012
KR    20130140303 A    * 12/2013 ............. C07C 15/14

OTHER PUBLICATIONS

Chemical Abstract Service STN Registry Nos. 1639407-38-7 and 1639407-31-0 [entered STN: Dec. 24, 2014].*
(Continued)

*Primary Examiner* — Amanda L Aguirre
(74) *Attorney, Agent, or Firm* — NSIP Law

(57) ABSTRACT

Disclosed is an organic light emitting compound represented by Formula I:

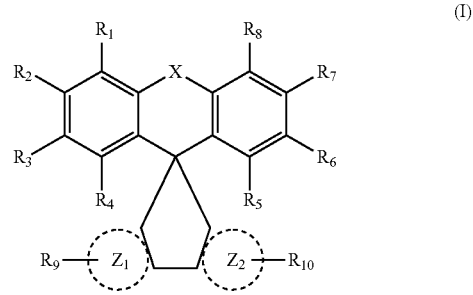

Also disclosed is an organic light emitting device including the organic light emitting compound. The organic light emitting device can be driven at a low voltage to achieve high power efficiency. In addition, the organic light emitting device has excellent luminescent properties, such as high (Continued)

luminance and high luminous efficiency. Due to these advantages, the organic light emitting device can be utilized as a display device or a lighting device.

4 Claims, 1 Drawing Sheet

(51) Int. Cl.
| | |
|---|---|
| *C07D 311/80* | (2006.01) |
| *C07D 311/92* | (2006.01) |
| *C07D 335/04* | (2006.01) |
| *C07D 335/10* | (2006.01) |
| *C07D 401/14* | (2006.01) |
| *C07D 405/14* | (2006.01) |
| *C07D 407/14* | (2006.01) |
| *C07D 409/14* | (2006.01) |
| *C07D 491/052* | (2006.01) |
| *C07D 491/10* | (2006.01) |
| *C07D 491/107* | (2006.01) |
| *C07D 491/20* | (2006.01) |
| *C07F 7/08* | (2006.01) |
| *C09K 11/06* | (2006.01) |
| *H01L 51/00* | (2006.01) |
| *H01L 51/50* | (2006.01) |
| *H01L 51/52* | (2006.01) |
| *H05B 33/14* | (2006.01) |
| *H05B 33/20* | (2006.01) |

(52) U.S. Cl.
CPC .......... *C07D 311/92* (2013.01); *C07D 335/04* (2013.01); *C07D 335/10* (2013.01); *C07D 401/14* (2013.01); *C07D 405/14* (2013.01); *C07D 407/14* (2013.01); *C07D 409/14* (2013.01); *C07D 491/052* (2013.01); *C07D 491/10* (2013.01); *C07D 491/107* (2013.01); *C07D 491/20* (2013.01); *C07F 7/0812* (2013.01); *C07F 7/0816* (2013.01); *C09K 11/06* (2013.01); *H01L 51/006* (2013.01); *H01L 51/0052* (2013.01); *H01L 51/0058* (2013.01); *H01L 51/0071* (2013.01); *H01L 51/0072* (2013.01); *H01L 51/0073* (2013.01); *H01L 51/0074* (2013.01); *H01L 51/0094* (2013.01); *H05B 33/14* (2013.01); *H05B 33/20* (2013.01); *C09K 2211/1007* (2013.01); *C09K 2211/1011* (2013.01); *C09K 2211/1014* (2013.01); *C09K 2211/1029* (2013.01); *C09K 2211/1033* (2013.01); *C09K 2211/1048* (2013.01); *C09K 2211/1088* (2013.01); *C09K 2211/1092* (2013.01); *C09K 2211/1096* (2013.01); *H01L 51/0061* (2013.01); *H01L 51/0067* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 51/5206* (2013.01); *H01L 51/5221* (2013.01); *H01L 2251/301* (2013.01); *H01L 2251/308* (2013.01); *H01L 2251/5361* (2013.01)

(58) Field of Classification Search
CPC ............ H01L 51/0073; H01L 51/0072; H01L 51/0058; H01L 51/0074; H01L 51/0071; H01L 51/006; H01L 51/0052; H01L 51/0061; H01L 51/5012; H01L 51/0067; C09K 11/06; C09K 2211/1007; C09K 2211/1014; C09K 2211/1011
See application file for complete search history.

(56) References Cited

OTHER PUBLICATIONS

Chemical Abstract Service STN Registry Database No. 1374847-14-9 [entered STN: May 31, 2012].*
Chemical Abstract Service STN Registry Database No. 1304132-56-6 [entered STN: Jun. 1, 2011].*
Chemical Abstract Service STN Registry Database No. 1639407-36-5 [entered STN: Dec. 24, 2014].*
Chemical Abstract Service STN, Registry Database [online], Registry No. 1589470-77-8, 1589470-76-7, 1589470-73-4, 1589470-72-3, 1589470-71-2, 1589470-65-4, and 1589470-64-3 [Entered STN: Apr. 24, 2014]. (Year: 2014).*
Chemical Abstract Service STN, Registry Database [online], Registry No. 1589470-62-1 and 1589470-60-9 [Entered STN Apr. 24, 2014]. (Year: 2014).*
Chemical Abstract Service STN, Registry Database [online], Registry No. 1639407-27-4 and 1639407-26-3 [Entered STN Dec. 24, 2014]. (Year: 2014).*
Xie et al. "Unexpected One-Pot Method to Synthesize Spiro[fluorene-9,9'-xanthene] Building Blocks for Blue-Light-Emitting Materials" Org. Lett. 2006, 8, 2787-2790. (Year: 2006).*
Chemical Abstract Service STN Registry Database Nos. 1639406-98-6, 1639406-97-5 [entered STN: Dec. 24, 2014]. (Year: 2014).*
Chemical Abstract Service STN Registry Database Nos. 1639407-48-9 [entered STN: Dec. 24, 2014]. (Year: 2014).*
Chemical Abstract Service STN Registry Database Nos. 1639928-44-1 [entered STN: Dec. 31, 2014]. (Year: 2014).*

\* cited by examiner
† cited by third party

| 80 |
|----|
| 70 |
| 60 |
| 50 |
| 40 |
| 30 |
| 20 |
| 10 |

ORGANIC LIGHT EMITTING COMPOUND AND ORGANIC LIGHT EMITTING DEVICE INCLUDING THE SAME

CROSS-REFERENCE TO RELATED APPLICATIONS

This application claims priority to Korean patent application KR 10-2014-0057851, filed May 14, 2014, which is incorporated herein in its entirety.

BACKGROUND OF THE INVENTION

1. Field of the Invention

The present invention relates to a novel organic light emitting compound and an organic light emitting device with excellent luminescent properties, such as high power efficiency and high luminance, including the organic light emitting compound.

2. Description of the Related Art

Materials for organic layers of organic light emitting devices can be classified into light emitting materials and charge transport materials by their functions. The charge transport materials may be, for example, hole injecting materials, hole transport materials, electron transport materials, and electron injecting materials. The light emitting materials are classified into blue, green, and red light emitting materials depending on what colors they emit. The light emitting materials also include yellow and orange light emitting materials necessary to obtain more natural colors.

A host/dopant system can be used as a light emitting material to increase the color purity of a light emitting layer and achieve increased luminescence efficiency of the light emitting layer through energy transfer. The host/dopant system is based on the principle that when a small amount of a dopant whose energy bandgap is smaller and whose luminescence efficiency is higher than those of a host essentially constituting the light emitting layer is mixed in the light emitting layer, excitons generated from the host are transported to the dopant to emit light with high efficiency. During this process, the wavelength of the host is shifted to the wavelength band of the dopant. Therefore, light with a desired wavelength can be obtained depending on the kind of the dopant used.

Stability and efficiency of materials for organic layers are prerequisites for the fabrication of organic light emitting devices with excellent characteristics. That is, organic light emitting devices should be supported by stable and efficient organic layer materials, for example, hole injecting materials, hole transport materials, light emitting materials, electron transport materials, and electron injecting materials, for their excellent characteristics. However, stable and efficient organic layer materials for organic light emitting devices remain at the early stage of development. There is thus a continued need to develop new materials for organic layers of organic light emitting devices.

SUMMARY OF THE INVENTION

Therefore, the present invention is directed to providing an organic light emitting compound suitable for use in the fabrication of an organic light emitting device with improved luminescent properties. The present invention is also directed to providing an organic light emitting device with excellent luminescent properties, such as high power efficiency and high luminance, including the organic light emitting compound.

One aspect of the present invention provides a novel organic light emitting compound represented by Formula I:

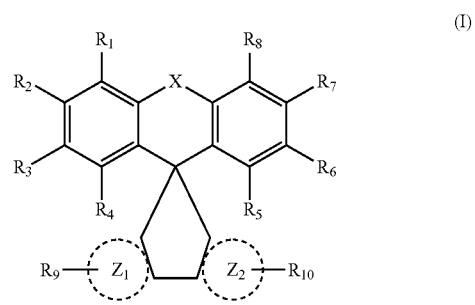

wherein the substituents are defined in detail below.

Another aspect of the present invention provides an organic light emitting device including the organic light emitting compound.

The organic light emitting device of the present invention can be driven at a low voltage, achieving high power efficiency. In addition, the organic light emitting device of the present invention has excellent luminescent properties, such as high luminance and high luminous efficiency. Due to these advantages, the organic light emitting device of the present invention can be utilized as a display device or a lighting device.

BRIEF DESCRIPTION OF THE DRAWINGS

These and/or other aspects and advantages of the invention will become apparent and more readily appreciated from the following description of the embodiments, taken in conjunction with the accompanying drawings of which:

The FIGURE is a schematic view of an organic light emitting device according to one embodiment of the present invention.

DETAILED DESCRIPTION OF THE INVENTION

The present invention will now be described in more detail.

The present invention provides an organic light emitting compound suitable for use in the fabrication of an organic light emitting device with improved luminescent properties, such as high power efficiency and high luminance. Particularly, the organic light emitting compound of the present invention is used as a host or dopant compound in a light emitting layer of an organic light emitting device.

Specifically, the organic light emitting compound of the present invention is represented by Formula I:

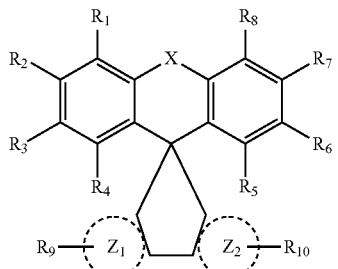

(I)

wherein X is $NR_{11}$, O, S or $SiR_{12}R_{13}$, $Z_1$ and $Z_2$ may be identical to or different from each other and may be each independently selected from monocyclic or polycyclic aromatic rings, monocyclic or polycyclic heteroaromatic rings, 5- and 6-membered heteroaromatic rings fused with an aromatic ring, and monocyclic or polycyclic aromatic rings fused with a 5- or 6-membered heteroaromatic ring, $R_1$ to $R_{13}$ may be identical to or different from each other and may be each independently selected from hydrogen, deuterium, substituted or unsubstituted $C_1$-$C_{30}$ alkyl groups, substituted or unsubstituted $C_5$-$C_{50}$ aryl groups, substituted or unsubstituted $C_2$-$C_{30}$ alkenyl groups, substituted or unsubstituted $C_2$-$C_{20}$ alkynyl groups, substituted or unsubstituted $C_3$-$C_{30}$ cycloalkyl groups, substituted or unsubstituted $C_2$-$C_{50}$ heteroaryl groups having one or more heteroatoms selected from O, N, S, and P, substituted or unsubstituted $C_1$-$C_{30}$ alkoxy groups, substituted or unsubstituted $C_6$-$C_{30}$ aryloxy groups, substituted or unsubstituted $C_1$-$C_{30}$ alkylthioxy groups, substituted or unsubstituted $C_5$-$C_{30}$ arylthioxy groups, substituted or unsubstituted $C_1$-$C_{30}$ alkylamine groups, substituted or unsubstituted $C_5$-$C_{30}$ arylamine groups, substituted or unsubstituted $C_1$-$C_{30}$ alkylsilyl groups, substituted or unsubstituted $C_5$-$C_{30}$ arylsilyl groups, cyano groups, nitro groups, hydroxyl groups, and halogen groups, with the proviso that $R_1$ to $R_{13}$ each may be optionally linked to the adjacent substituent to form an alicyclic or aromatic monocyclic or polycyclic ring whose carbon atoms may be optionally substituted with one or more heteroatoms selected from N, S, and O.

According to one embodiment of the present invention, $R_1$ to $R_{13}$ in Formula I may be optionally further substituted with one or more substituents selected from deuterium, cyano groups, halogen groups, hydroxyl groups, nitro groups, $C_1$-$C_{24}$ alkyl groups, $C_1$-$C_{24}$ halogenated alkyl groups, $C_1$-$C_{24}$ alkenyl groups, $C_1$-$C_{24}$ alkynyl groups, $C_3$-$C_{24}$ cycloalkyl groups, $C_6$-$C_{24}$ aryl groups, $C_6$-$C_{24}$ arylalkyl groups, $C_2$-$C_{24}$ heteroaryl groups, $C_1$-$C_{24}$ alkoxy groups, $C_1$-$C_{24}$ alkylamino groups, $C_3$-$C_{24}$ arylamino groups, $C_1$-$C_{24}$ alkylsilyl groups, $C_3$-$C_{24}$ arylsilyl groups, and $C_3$-$C_{24}$ aryloxy groups.

According to a preferred embodiment of the present invention,

may be identical to or different from and may be each independently selected from the following structures C1 to C15:

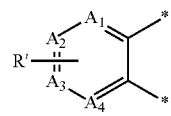

C1

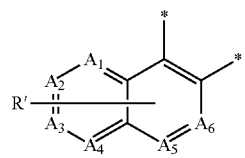

C2

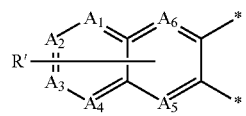

C3

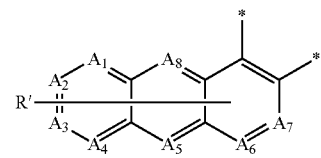

C4

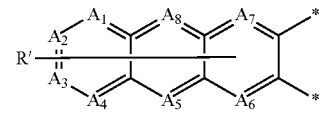

C5

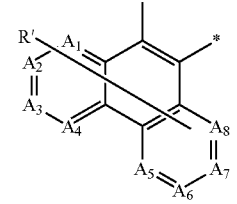

C6

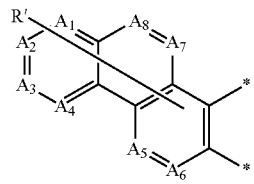

C7

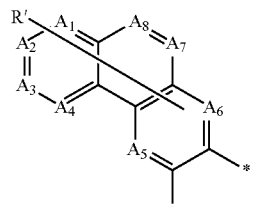

C8

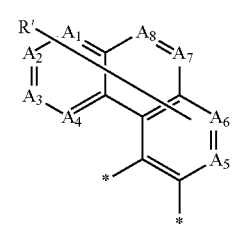

C9

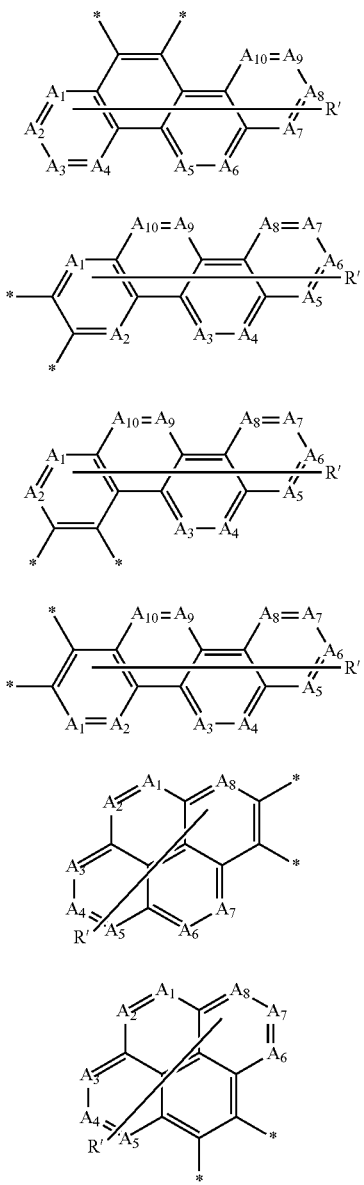

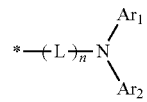

wherein $A_1$ to $A_{10}$ are identical to or different from each other and are each independently N or CR, R and R' are as defined in Formula I, and * indicates a site at which the corresponding structure is bonded to the skeleton of Formula I.

In Formula I, $R_1$ to $R_{10}$ may be identical to or different from each other. More specifically, $R_1$ to $R_{10}$ may be each independently selected from hydrogen, deuterium, halogens, hydroxyl groups, cyano groups, nitro groups, substituted or unsubstituted $C_1$-$C_{20}$ alkyl groups, substituted or unsubstituted $C_3$-$C_{30}$ cycloalkyl groups, substituted or unsubstituted $C_2$-$C_{20}$ alkenyl groups, substituted or unsubstituted $C_2$-$C_{20}$ alkynyl groups, substituted or unsubstituted $C_5$-$C_{50}$ aryl groups, substituted or unsubstituted $C_2$-$C_{50}$ heteroaryl groups, and the following structure Q:

wherein * indicates a site at which the structure is bonded to the skeleton of Formula I, L may be selected from substituted or unsubstituted $C_1$-$C_{60}$ alkylene groups, substituted or unsubstituted $C_2$-$C_{60}$ alkenylene groups, substituted or unsubstituted $C_2$-$C_{60}$ alkynylene groups, substituted or unsubstituted $C_3$-$C_{60}$ cycloalkylene groups, substituted or unsubstituted $C_5$-$C_{50}$ arylene groups, substituted or unsubstituted $C_2$-$C_{50}$ heteroarylene groups, substituted or unsubstituted $C_6$-$C_{60}$ arylene groups fused with one or more substituted or unsubstituted $C_3$-$C_{30}$ cycloalkyl groups, and substituted or unsubstituted $C_2$-$C_{60}$ heteroarylene groups fused with one or more substituted or unsubstituted $C_3$-$C_{30}$ cycloalkyl groups, n is an integer from 0 to 2, provided that when n is 2, the two moieties L may be identical to or different from each other, and $Ar_1$ and $Ar_2$ may be identical to or different from each other and may be each independently selected from substituted or unsubstituted $C_1$-$C_{30}$ alkyl groups, substituted or unsubstituted $C_3$-$C_{30}$ cycloalkyl groups, substituted or unsubstituted $C_5$-$C_{50}$ aryl groups, and substituted or unsubstituted $C_2$-$C_{50}$ heteroaryl groups having one or more heteroatoms selected from O, N, S, and P, with the proviso that $Ar_1$ and $Ar_2$ may be linked to each other or $Ar_1$ and $Ar_2$ each may be linked to the adjacent substituent to form an aliphatic, aromatic, heteroaliphatic or heteroaromatic fused ring.

$R_9$ and $R_{10}$ in Formula I may be identical to or different from each other and are each independently the structure Q.

In the structure Q, the amine group (*—NAr1Ar2) including $Ar_1$ and $Ar_2$ may be selected from the following substituents B1 to B46:

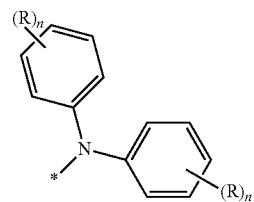

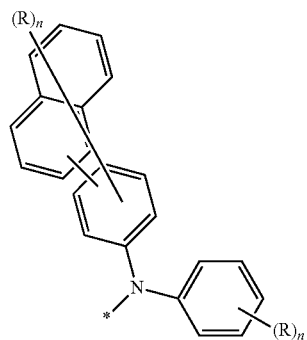

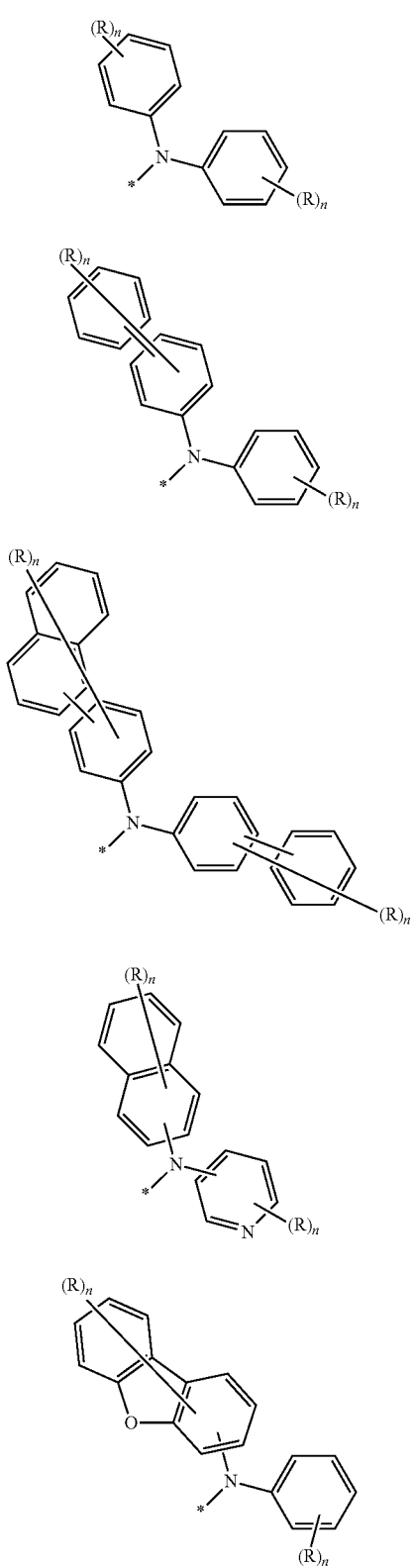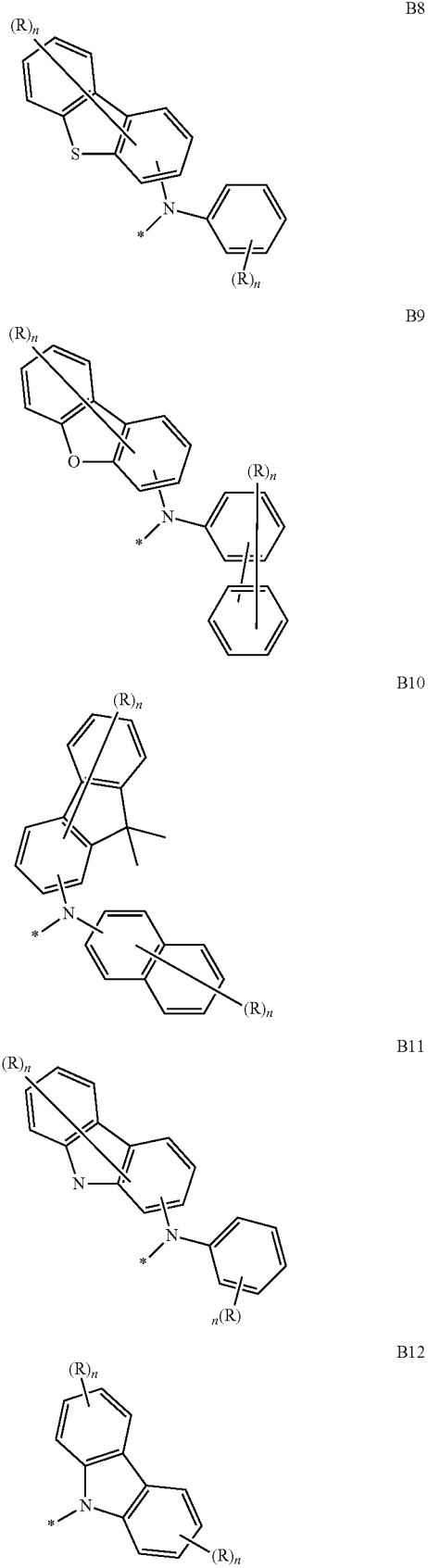

B13 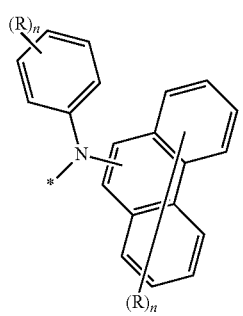
B14 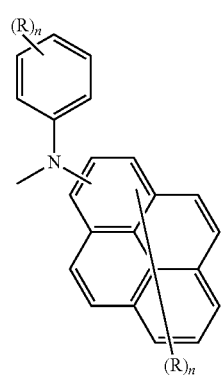
B15 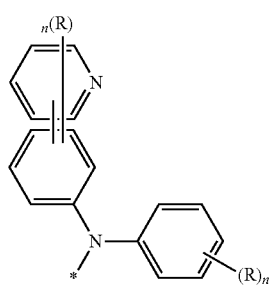
B16 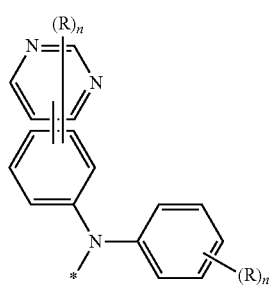
B17 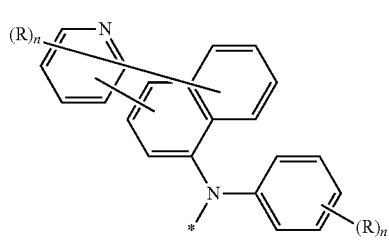
B18 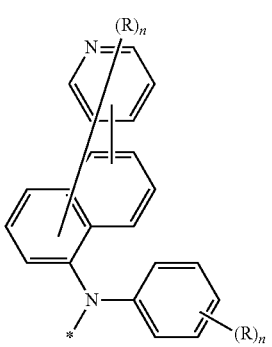
B19 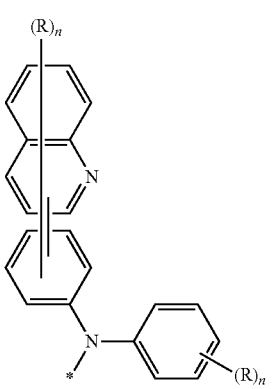
B20 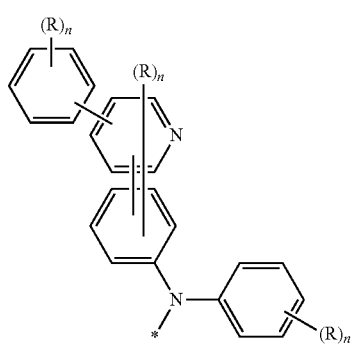
B21 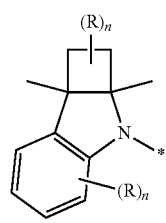
B22

-continued
B23 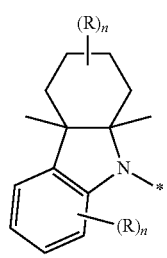
B24 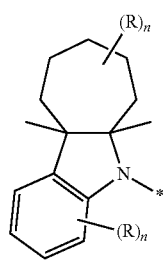
B25 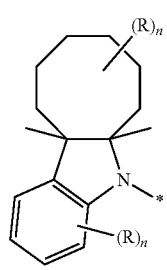
B26 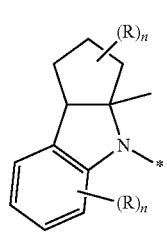
B27 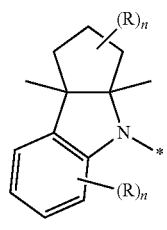
B28 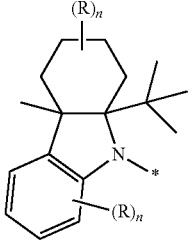
-continued
B29 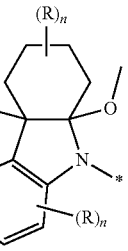
B30 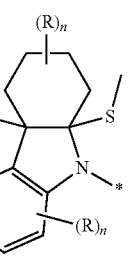
B31 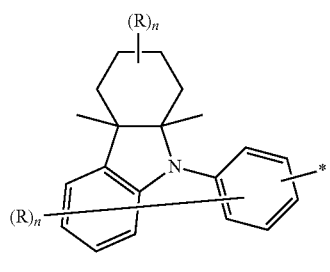
B32 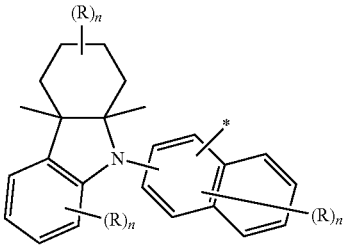
B33 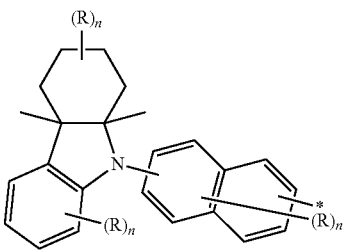
B34 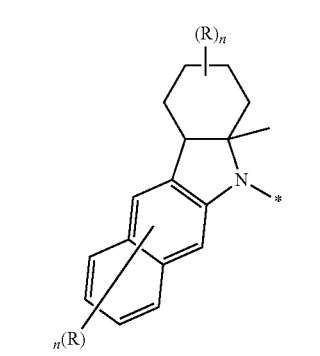

-continued
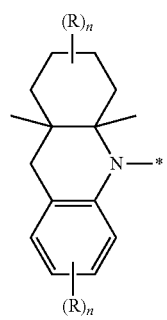
B35
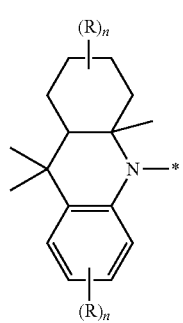
B36
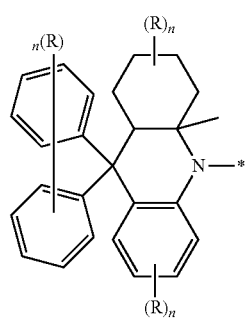
B37
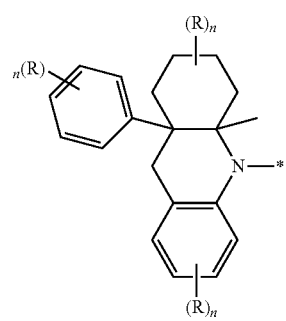
B38
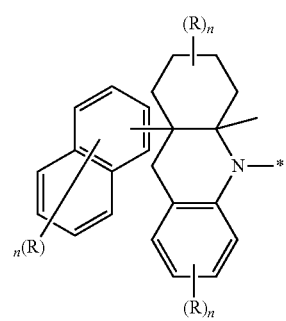
B39
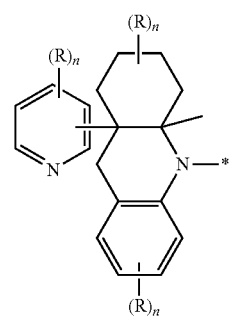
B40
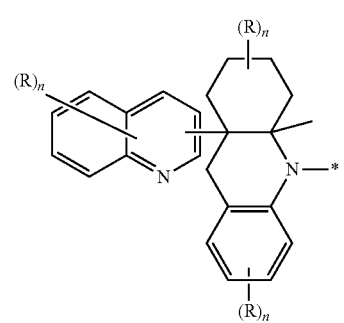
B41
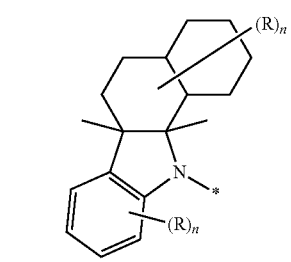
B42
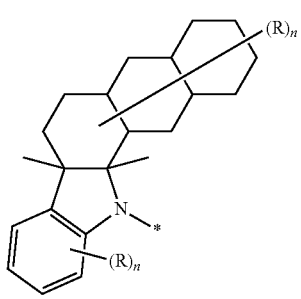
B43
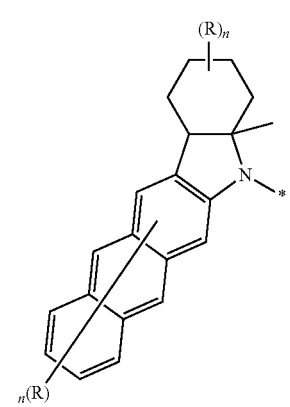
B44

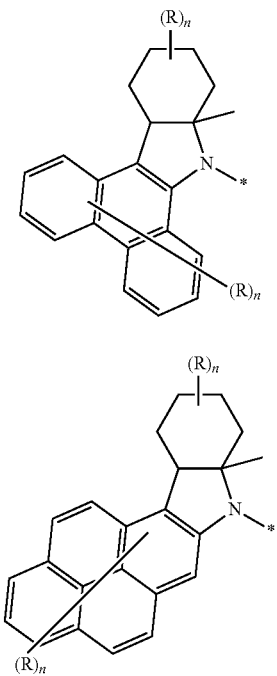

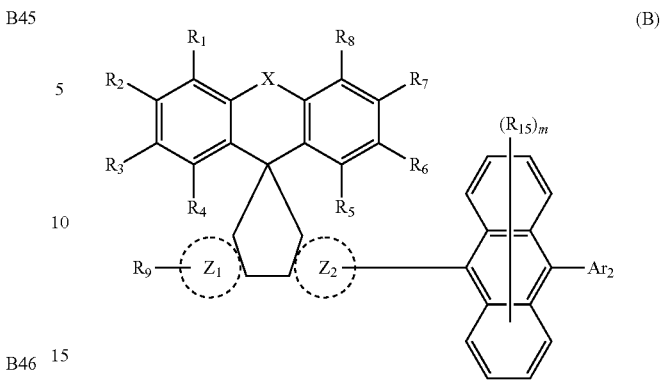

In Substituents B1 to B46, R may be selected from hydrogen, deuterium, cyano groups, halogen groups, $C_1$-$C_6$ alkyl groups, $C_6$-$C_{18}$ aryl groups, $C_6$-$C_{18}$ arylalkyl groups, $C_3$-$C_{18}$ heteroaryl groups, $C_1$-$C_{12}$ alkylsilyl groups, $C_6$-$C_{18}$ arylsilyl groups, substituted or unsubstituted $C_1$-$C_6$ alkoxy groups, and substituted or unsubstituted $C_6$-$C_{18}$ aryloxy groups, n is an integer from 0 to 12, provided that when n is greater than or equal to 2, the groups R may be identical to or different from each other and each may be fused with the adjacent substituent to form a ring.

More specifically, the organic light emitting compound of Formula I may be selected from compounds represented by Formulae A and B:

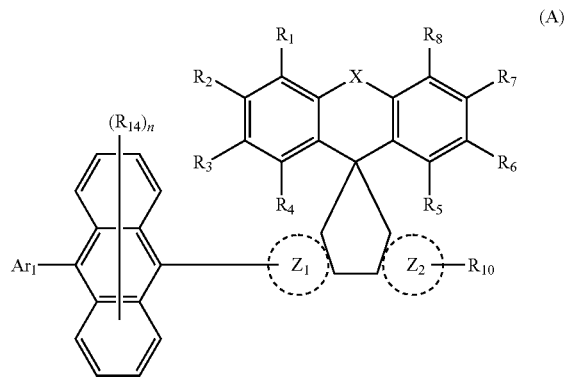

wherein X, $Z_1$, $Z_2$, and $R_1$ to $R_{13}$ are as defined in Formula I, $Ar_1$ and $Ar_2$ may be identical to or different from each other and may be each independently selected from substituted or unsubstituted $C_1$-$C_{30}$ alkyl groups, substituted or unsubstituted $C_3$-$C_{30}$ cycloalkyl groups, substituted or unsubstituted $C_5$-$C_{50}$ aryl groups, and substituted or unsubstituted $C_2$-$C_{50}$ heteroaryl groups having one or more heteroatoms selected from O, N, S, and P, $R_{14}$ and $R_{15}$ have the same meanings as $R_1$ to $R_{13}$ defined in Formula I, and n and m are each independently an integer from 1 to 8, provided that when n is greater than or equal to 2, the groups $R_{14}$ are identical to or different from each other and when m is greater than or equal to 2, the groups $R_{15}$ are identical to or different from each other.

The aryl groups used as substituents in the compound of the present invention are organic radicals derived from aromatic hydrocarbons by removal of one hydrogen atom. Such aryl groups include 5- to 7-membered, preferably 5- or 6-membered single or fused ring systems. When substituted, each aryl group may be optionally fused with the adjacent substituent to form a ring.

Specific examples of the aryl groups include aromatic groups, such as phenyl, 2-methylphenyl, 3-methylphenyl, 4-methylphenyl, 4-ethylphenyl, o-biphenyl, m-biphenyl, p-biphenyl, 4-methylbiphenyl, 4-ethylbiphenyl, o-terphenyl, m-terphenyl, p-terphenyl, 1-naphthyl, 2-naphthyl, 1-methylnaphthyl, 2-methylnaphthyl, anthryl, phenanthryl, pyrenyl, indenyl, fluorenyl, tetrahydronaphthyl, perylenyl, crycenyl, naphthacenyl, and fluoranthenyl groups.

At least one hydrogen atom of each aryl group may be substituted with a deuterium atom, a halogen atom, a hydroxyl group, a nitro group, a cyano group, a silyl group, an amino group ($—NH_2$, $—NH(R)$, $—N(R')(R'')$) in which R, R' and R'' are each independently a $C_1$-$C_{10}$ alkyl group (the $—NH(R)$ and $—N(R')(R'')$ are referred to as "alkylamino groups"), an amidino group, a hydrazine group, a hydrazone group, a carboxyl group, a sulfonic acid group, a phosphoric acid group, a $C_1$-$C_{24}$ alkyl group, a $C_1$-$C_{24}$ halogenated alkyl group, a $C_1$-$C_{24}$ alkenyl group, a $C_1$-$C_{24}$ alkynyl group, a C1-C24 heteroalkyl group, a $C_6$-$C_{24}$ aryl group, a $C_6$-$C_{24}$ arylalkyl group, a $C_2$-$C_{24}$ heteroaryl group or a $C_2$-$C_{24}$ heteroarylalkyl group.

The heteroaryl groups used as substituents in the compound of the present invention may be selected from the following structures 1 to 6:

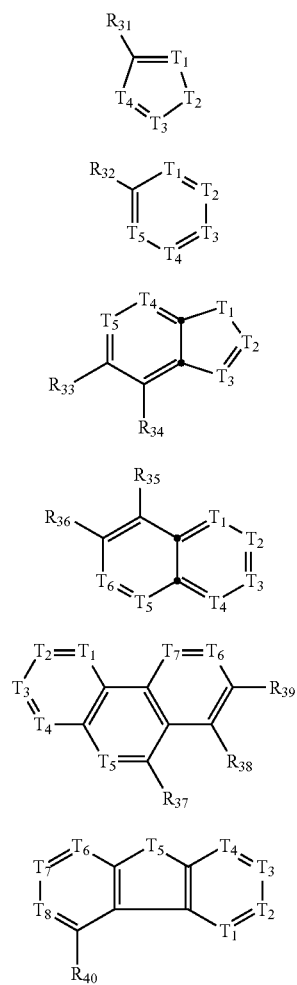

(1)
(2)
(3)
(4)
(5)
(6)

wherein $T_1$ to $T_8$ may be identical to or different from each other and may be each independently selected from $C(R_{41})$, $C(R_{42})(R_{43})$, N, $N(R_{44})$, O, and S, $R_{31}$ to $R_{44}$ may be identical to or different from each other and may be each independently selected from hydrogen, deuterium substituted or unsubstituted $C_1$-$C_{30}$ alkyl groups, substituted or unsubstituted $C_3$-$C_{30}$ cycloalkyl groups, substituted or unsubstituted $C_5$-$C_{50}$ aryl groups, and substituted or unsubstituted $C_2$-$C_{50}$ heteroaryl groups having one or more heteroatoms selected from O, N, and S, with the proviso that one of $R_{31}$ to $R_{44}$ may be bonded to the nitrogen in Formula I to form a single bond.

Due to resonance resulting from the migration of electrons, Structure 3 may also be represented by the following structure 3-1:

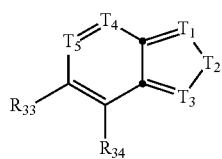

(3-1)

wherein $T_1$ to $T_5$ and $R_{33}$ to $R_{34}$ are as defined in Structure 3.

According to a preferred embodiment of the present invention, Structures 1 to 6 may be selected from the following structures 7:

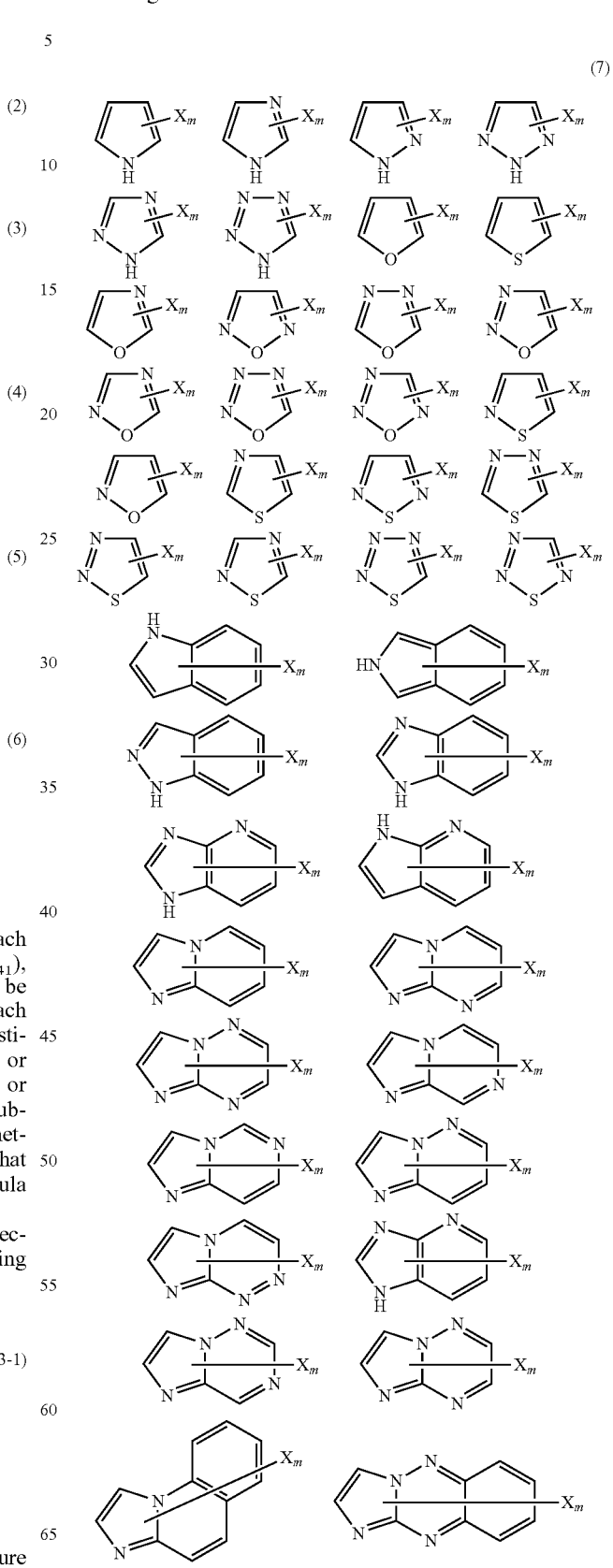

(7)

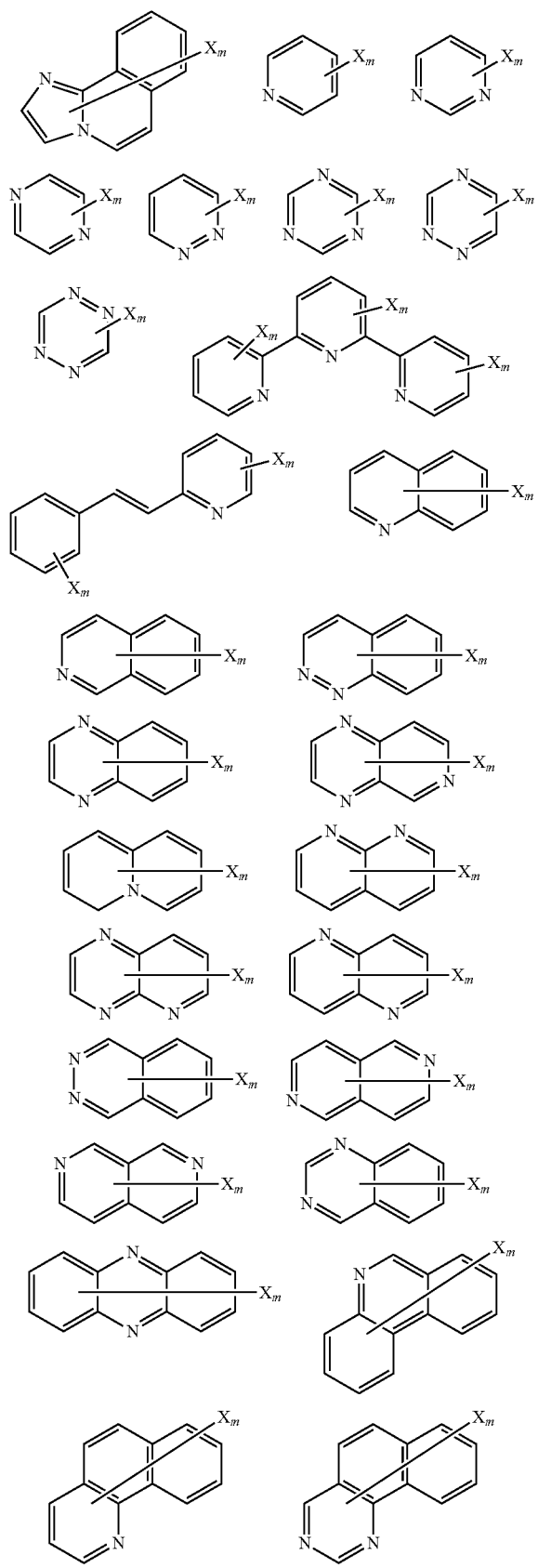
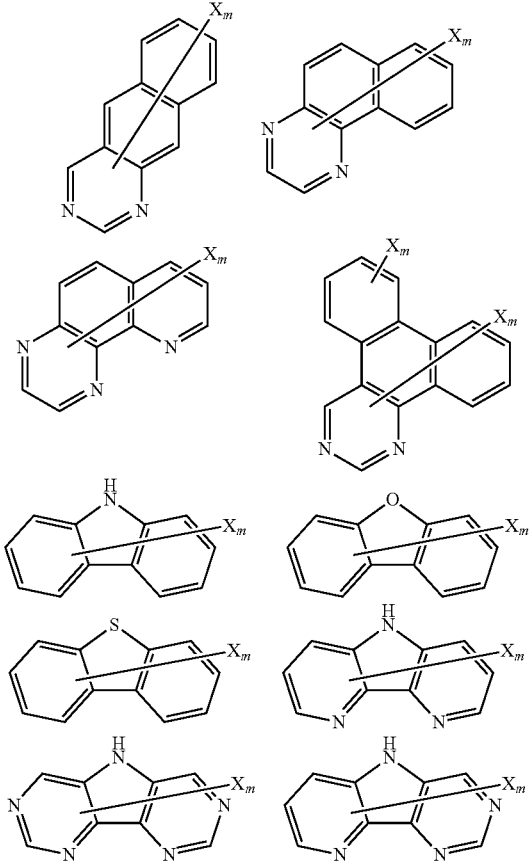

wherein X is selected from the group consisting of hydrogen, deuterium, substituted or unsubstituted $C_1$-$C_{30}$ alkyl groups, substituted or unsubstituted $C_5$-$C_{30}$ aryl groups, substituted or unsubstituted $C_2$-$C_{30}$ alkenyl groups, substituted or unsubstituted $C_2$-$C_{20}$ alkynyl groups, substituted or unsubstituted $C_3$-$C_{30}$ cycloalkyl groups, substituted or unsubstituted $C_5$-$C_{30}$ cycloalkenyl groups, substituted or unsubstituted alkoxy groups, substituted or unsubstituted $C_6$-$C_{30}$ aryloxy groups, substituted or unsubstituted $C_1$-$C_{30}$ alkylthioxy groups, substituted or unsubstituted $C_5$-$C_{30}$ arylthioxy groups, substituted or unsubstituted $C_1$-$C_{30}$ alkylamine groups, substituted or unsubstituted $C_5$-$C_{50}$ aryl groups, substituted or unsubstituted $C_2$-$C_{30}$ heteroaryl groups having one or more heteroatoms selected from O, N, S, and P, cyano groups, nitro groups, and halogen groups, m is an integer from 1 to 11, provided that when m is greater than or equal to 2, the groups X are identical to or different from each other and one of the groups X may be linked to one of $R_1$ to $R_{10}$, $Z_1$, $Z_2$ and their substituents in Formula I to form a single bond.

Specific examples of the alkyl groups as substituents suitable for use in the compound of the present invention include methyl, ethyl, propyl, isobutyl, sec-butyl, tert-butyl, pentyl, iso-amyl, hexyl, heptyl, octyl, stearyl, trichloromethyl, and trifluoromethyl groups. At least one hydrogen atom of each alkyl group may be substituted with a deuterium atom, a halogen atom, a hydroxyl group, a nitro group, a cyano group, a trifluoromethyl group, a silyl group (herein referred to as an "alkylsilyl group"), a substituted or unsubstituted amino group (—$NH_2$, —NH(R) or —N(R')(R")), in which R, R', and R" are each independently a $C_1$-$C_{24}$ alkyl group (the —NH(R) and —N(R')(R") are referred to as "alkylamino groups"), an amidino group, a hydrazine group, a hydrazone group, a carboxyl group, a sulfonic acid group, a phosphoric acid group, a $C_1$-$C_{24}$ alkyl group, a $C_1$-$C_{24}$ halogenated alkyl group, a $C_2$-$C_{24}$ alkenyl group, a $C_2$-$C_{24}$ alkynyl group, a $C_1$-$C_{24}$ heteroalkyl group, a $C_5$-$C_{24}$ aryl group, a $C_6$-$C_{24}$ arylalkyl group, a $C_3$-$C_{24}$ heteroaryl group or a $C_3$-$C_{24}$ heteroarylalkyl group.

Specific examples of the alkoxy groups as substituents suitable for use in the compound of the present invention include methoxy, ethoxy, propoxy, isobutyloxy, sec-butyloxy, pentyloxy, iso-amyloxy, and hexyloxy groups. The alkoxy groups may be substituted with the same substituents as in the alkyl groups.

Specific examples of the halogen groups as substituents suitable for use in the compound of the present invention include fluoro (F), chloro (Cl), and bromo (Br) groups.

The aryloxy groups used as substituents in the compound of the present invention refer to —O-aryl radicals in which the aryl group is as defined above. Specific examples of the aryloxy groups include phenoxy, naphthoxy, anthracenyloxy, phenanthrenyloxy, fluorenyloxy, and indenyloxy. At least one hydrogen atom of each aryloxy group may be substituted.

Specific examples of the silyl groups as substituents suitable for use in the compound of the present invention include trimethylsilyl, triethylsilyl, triphenylsilyl, trimethoxysilyl, dimethoxyphenylsilyl, diphenylmethyl silyl, diphenylvinylsilyl, methylcyclobutylsilyl, and dimethylfurylsilyl.

The alkenyl groups used as substituents in the compound of the present invention are straight or branched alkenyl groups, and specific examples thereof include 3-pentenyl, 4-hexenyl, 5-heptenyl, 4-methyl-3-pentenyl, 2,4-dimethylpentenyl, 6-methyl-5-heptenyl, and 2,6-dimethyl-5-heptenyl groups.

The term "substituted" in the definition of "substituted or unsubstituted" used herein refers to substitution with at least one substituent selected from the group consisting of deuterium, cyano groups, halogen groups, hydroxyl groups, nitro groups, $C_1$-$C_{24}$ alkyl groups, $C_1$-$C_{24}$ halogenated alkyl groups, $C_1$-$C_{24}$ alkenyl groups, $C_1$-$C_{24}$ alkynyl groups, $C_1$-$C_{24}$ heteroalkyl groups, $C_6$-$C_{24}$ aryl groups, $C_6$-$C_{24}$ arylalkyl groups, $C_2$-$C_{24}$ heteroaryl groups, $C_2$-$C_{24}$ heteroarylalkyl groups, $C_1$-$C_{24}$ alkoxy groups, $C_1$-$C_{24}$ alkylamino groups, $C_1$-$C_{24}$ arylamino groups, $C_1$-$C_{24}$ heteroarylamino groups, $C_1$-$C_{24}$ alkylsilyl groups, $C_1$-$C_{24}$ arylsilyl groups, $C_1$-$C_{24}$ aryloxy groups, germanium, phosphorus, and boron.

In the "substituted or unsubstituted $C_1$-$C_{30}$ alkyl groups", "substituted or unsubstituted $C_5$-$C_{50}$ aryl groups", etc., the number of carbon atoms in each substituted or unsubstituted alkyl or aryl group indicates the number of carbon atoms constituting the unsubstituted alkyl or aryl moiety without considering the number of carbon atoms in the substituent(s). For example, a phenyl group substituted with a butyl group at the para-position corresponds to a $C_6$ aryl group substituted with a $C_4$ butyl group.

According to preferred embodiments of the present invention, the organic light emitting compound of Formula I may be selected from the following compounds 1 to 60:

Compound 1

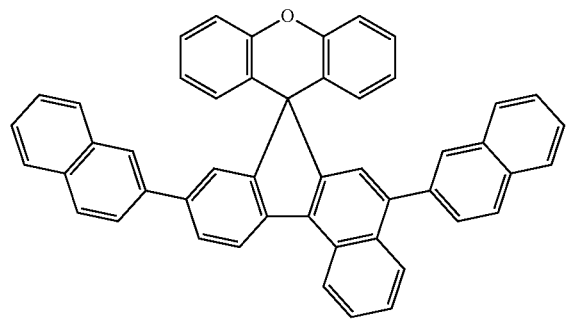

Compound 2

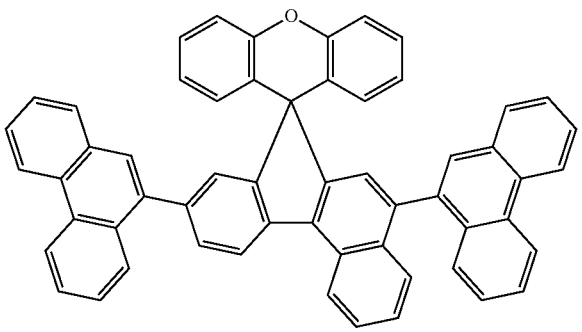

Compound 3

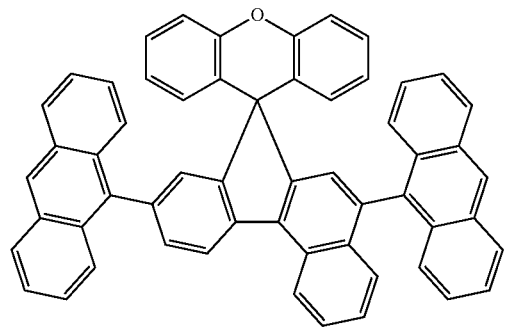

Compound 4

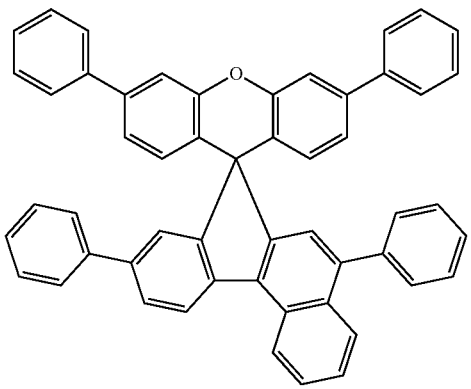

Compound 5
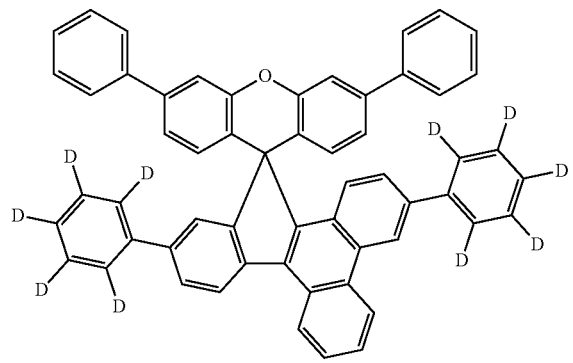
Compound 6
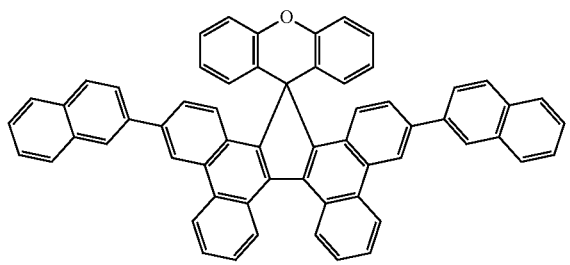
Compound 7
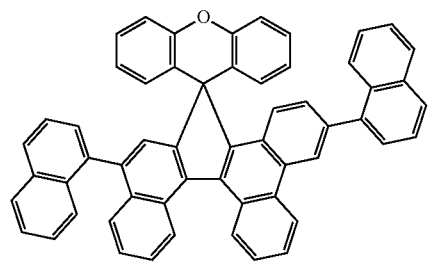
Compound 8
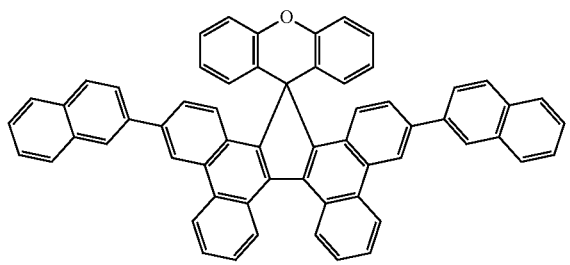
Compound 9
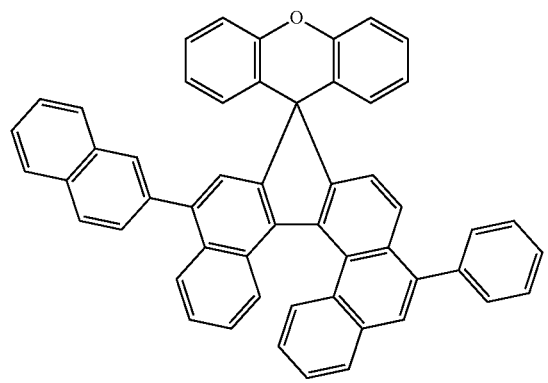
Compound 10
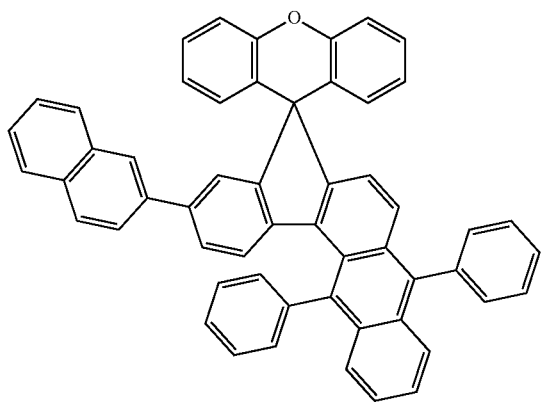
Compound 11
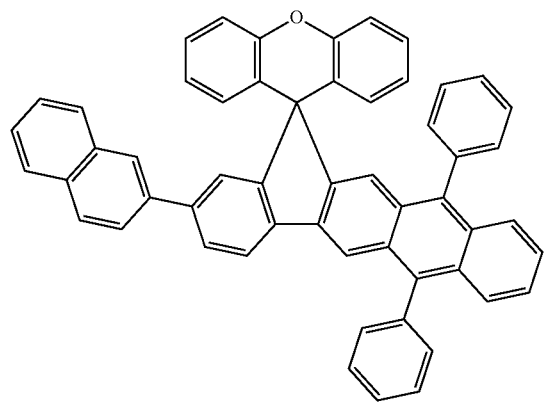
Compound 12
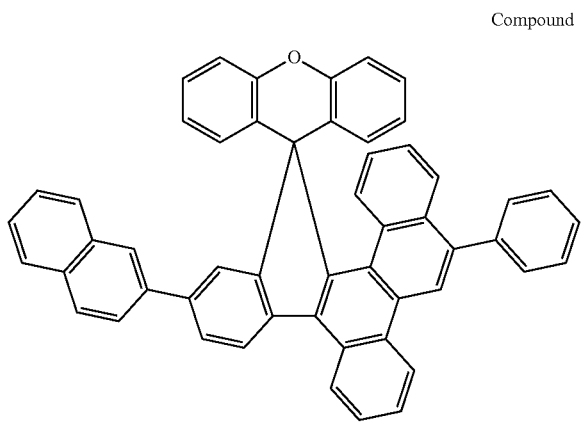

-continued
Compound 13
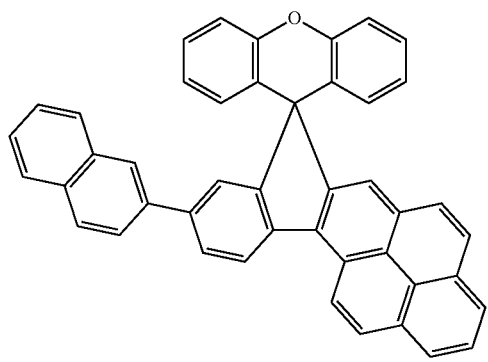
Compound 14
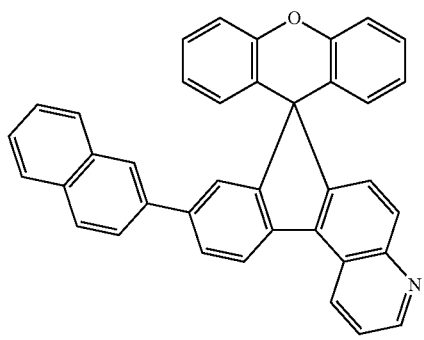
Compound 15
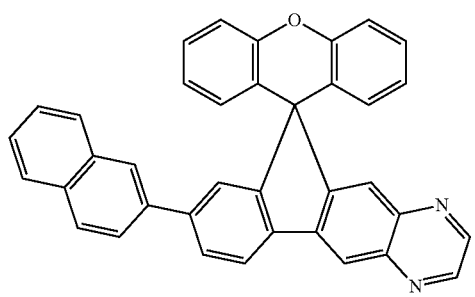
Compound 16
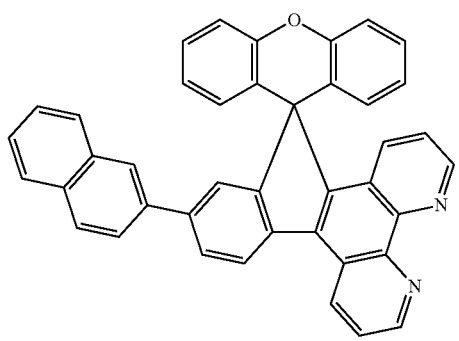
Compound 17
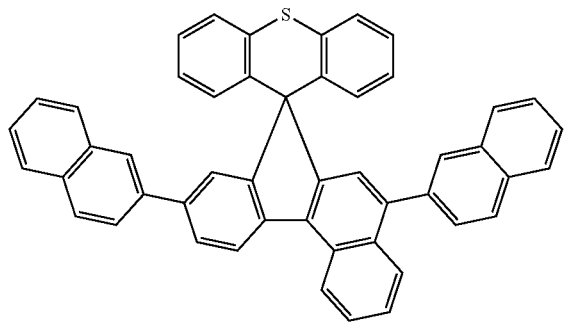
Compound 18
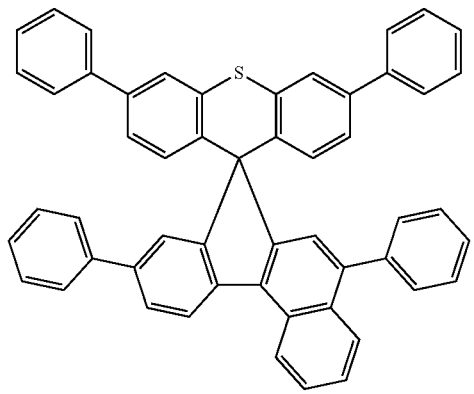
Compound 19
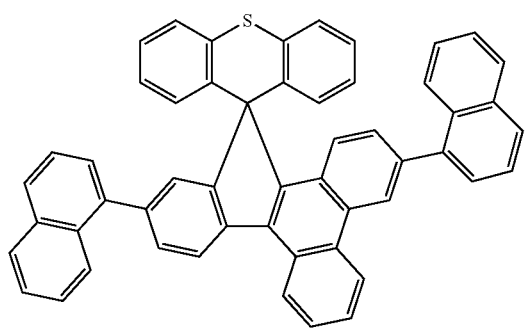
Compound 20
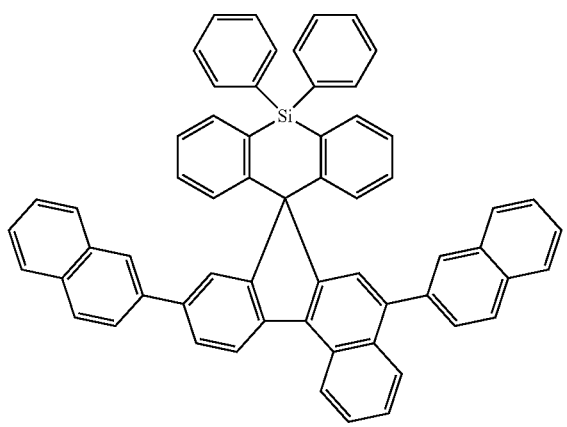

-continued
Compound 21
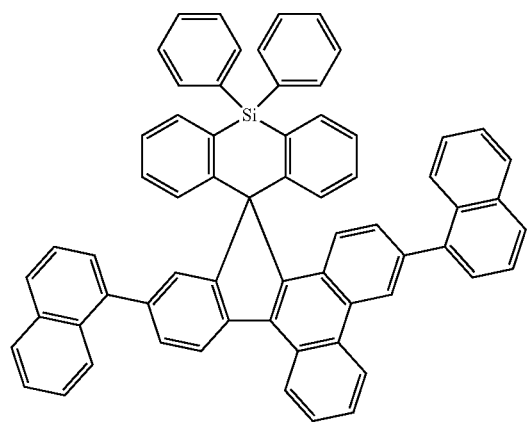
Compound 22
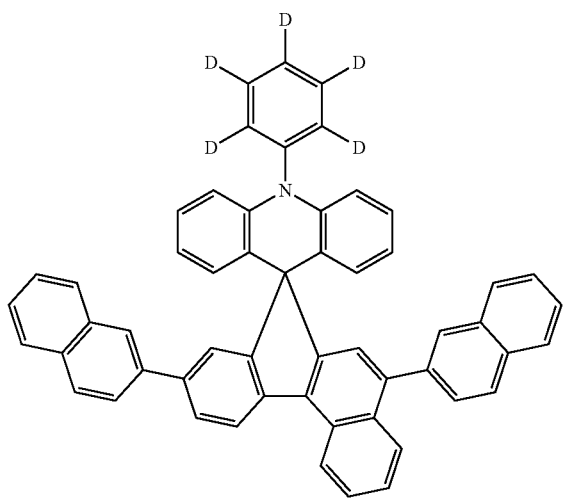
Compound 23
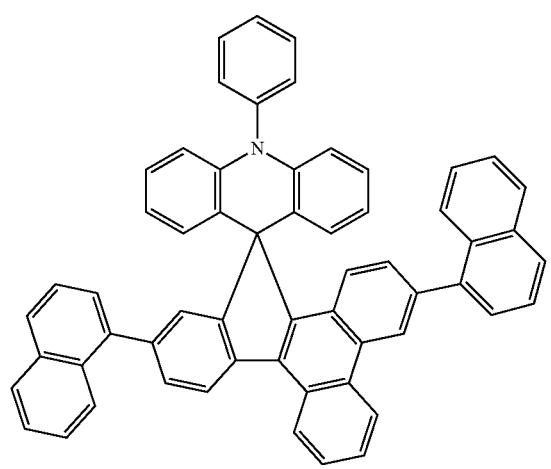
Compound 24
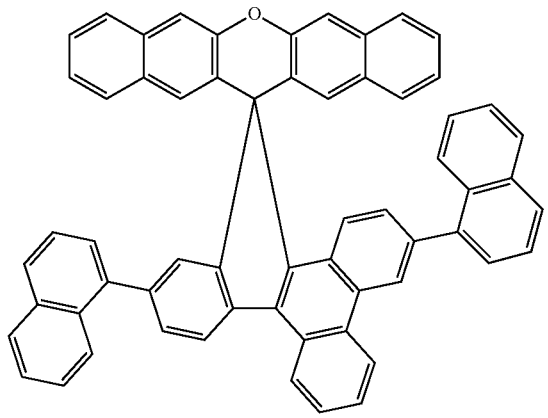
Compound 25
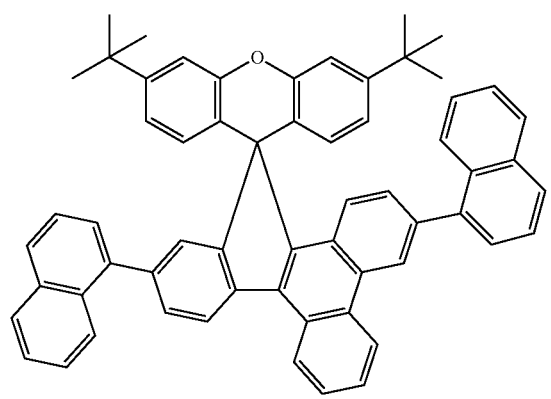
Compound 26
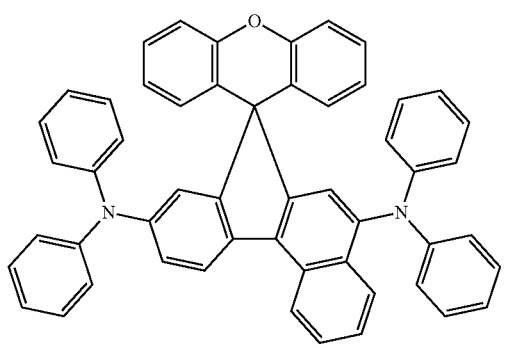

-continued
Compound 27
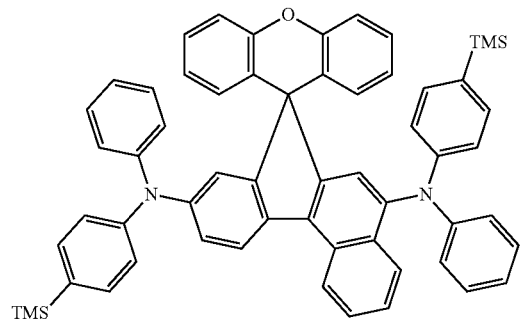
Compound 28
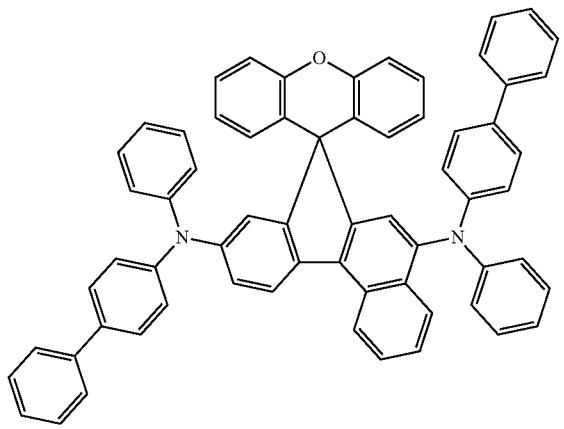
Compound 29
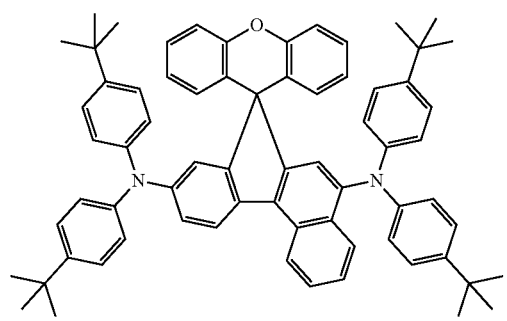
Compound 30
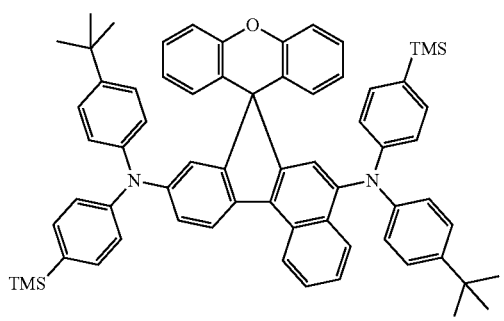
Compound 31
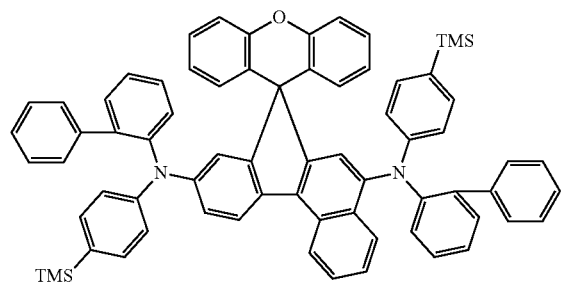
Compound 32
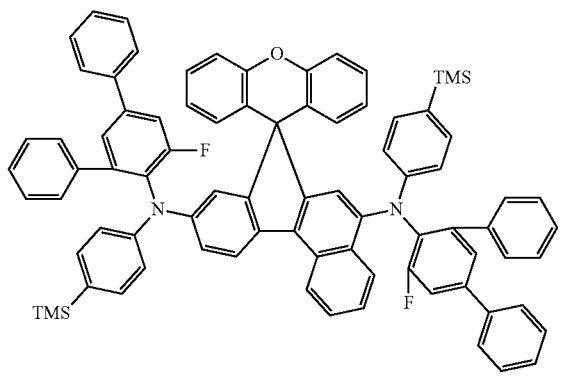
Compound 33
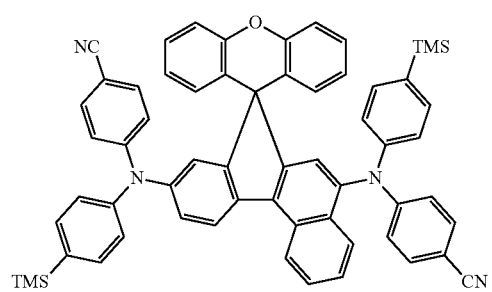
Compound 34
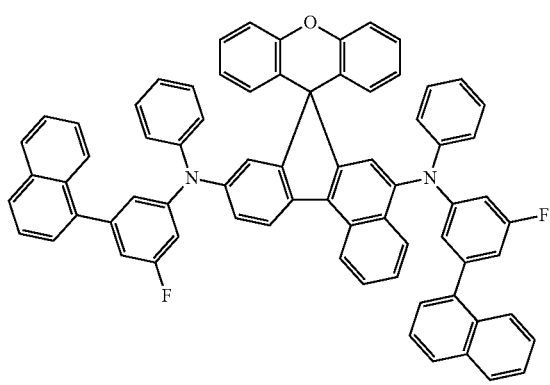

-continued
Compound 35
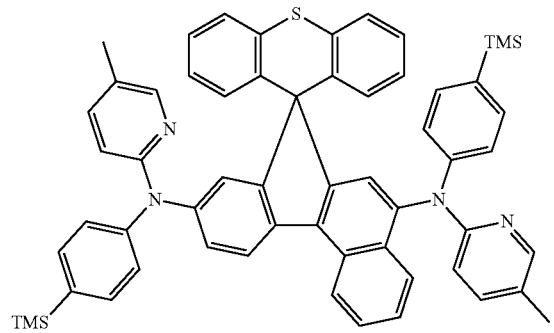
Compound 36
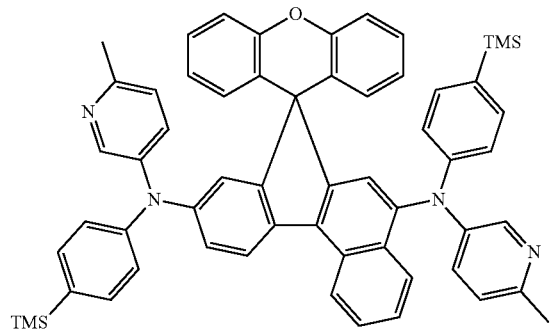
Compound 37
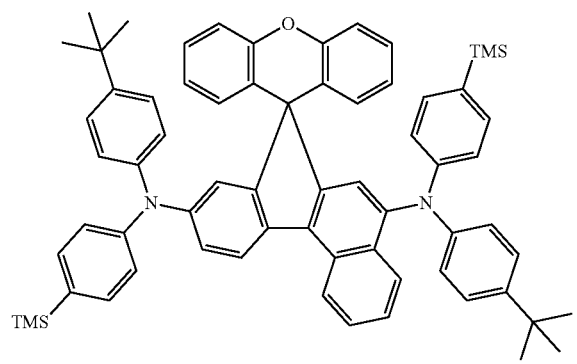
Compound 38
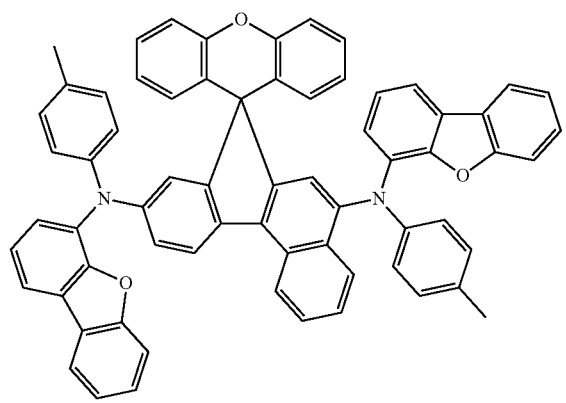
Comopund 39
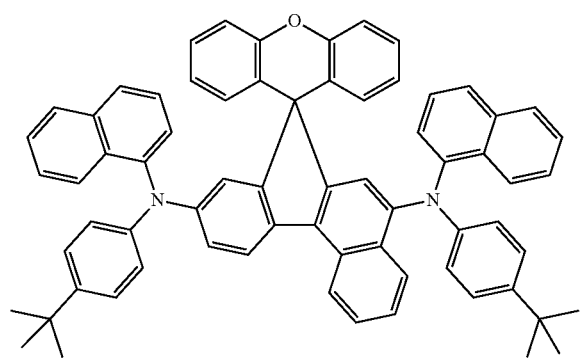
Compound 40
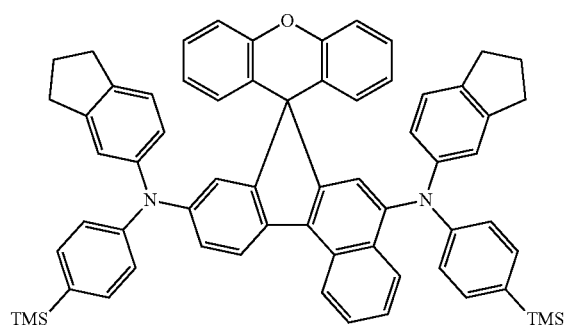
Compound 38
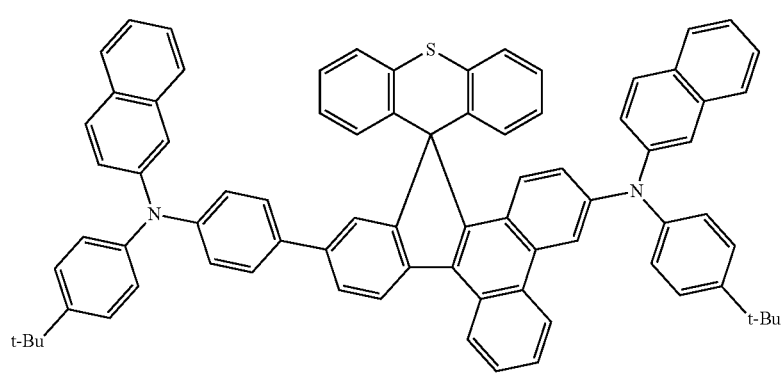

-continued
Compound 42
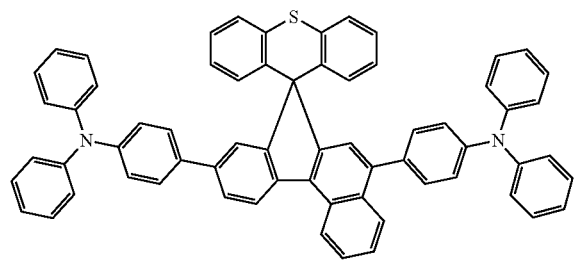
Compound 43
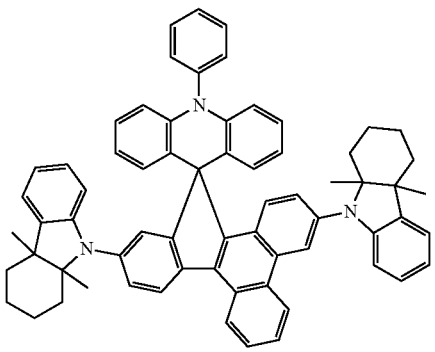
Compound 44
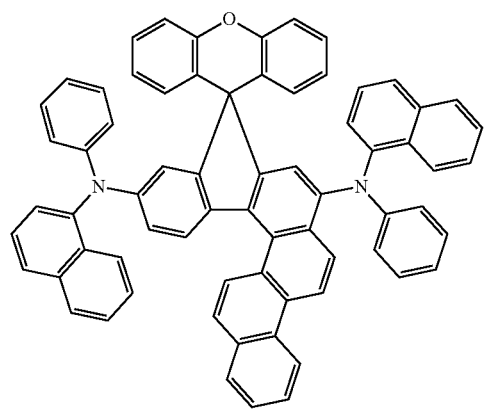
Compound 45
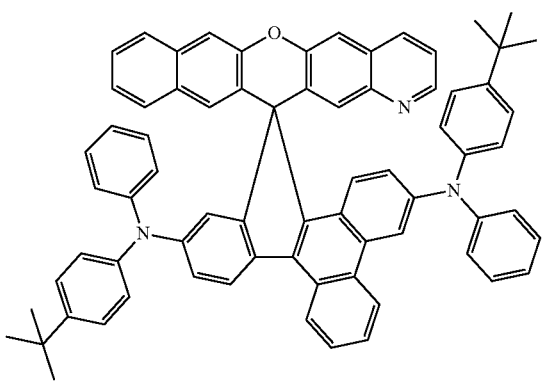
Compound 46
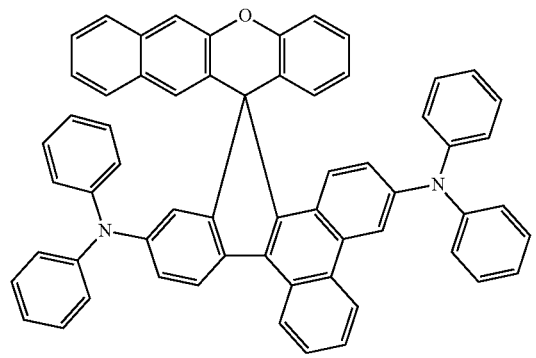
Compound 47
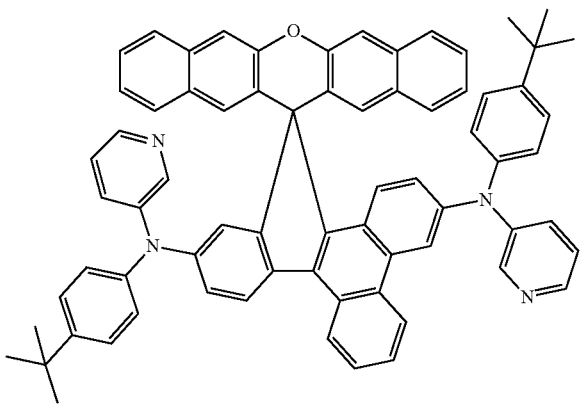
Compound 48
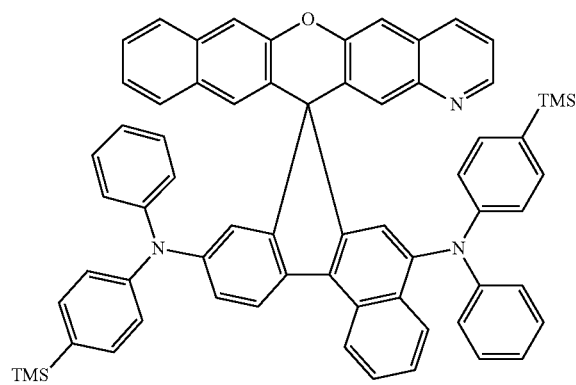
Compound 49
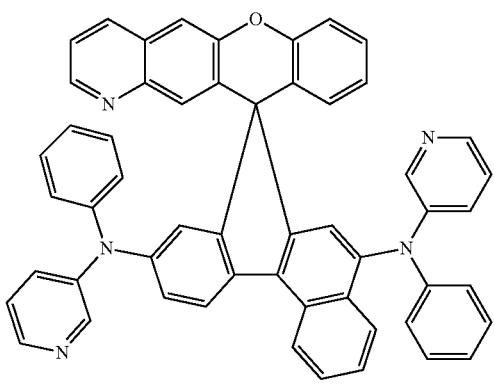

-continued
Compound 50
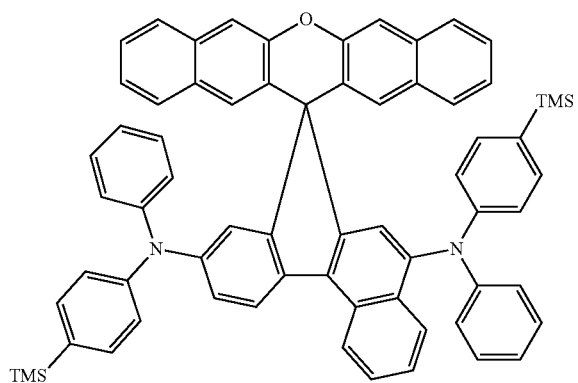
Compound 51
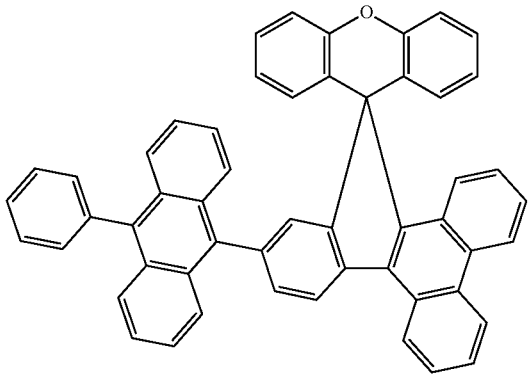
Compound 52
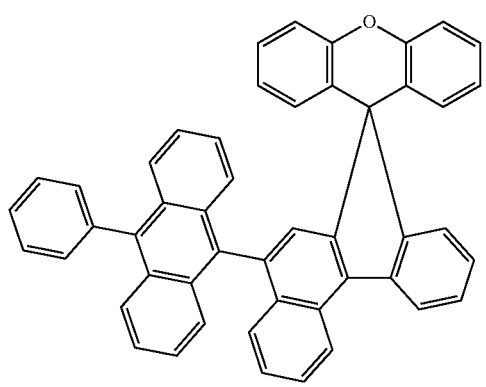
Compond 53
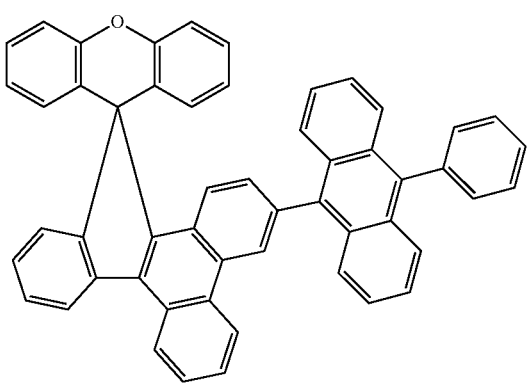
Compound 54
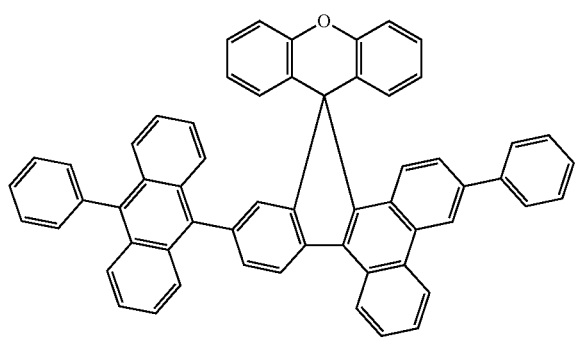
Compound 55
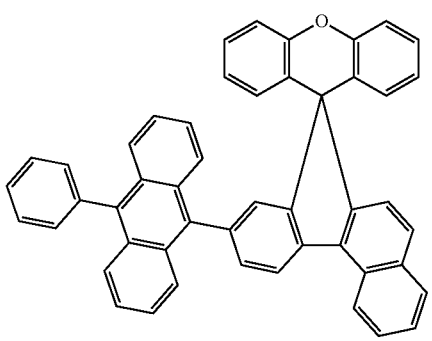
Compound 56
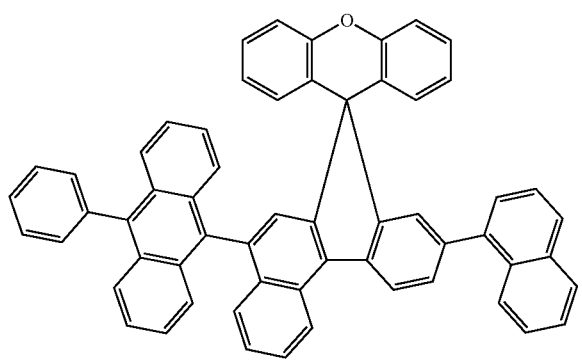
Compound 57
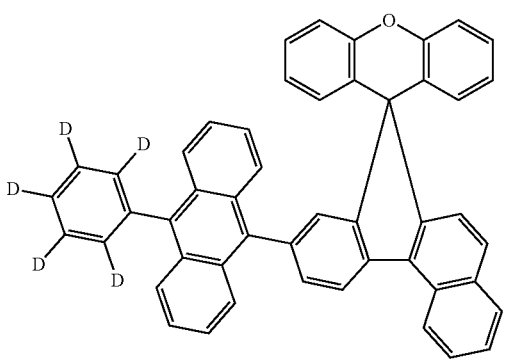

Compound 58

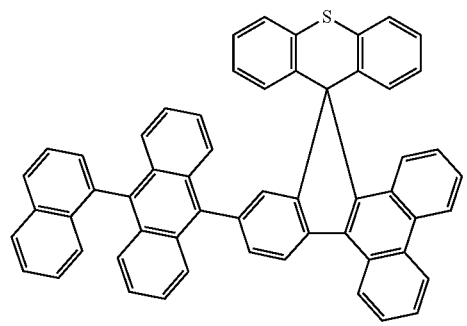

Compound 59

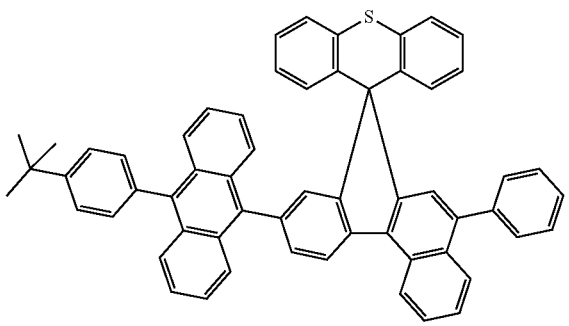

Compound 60

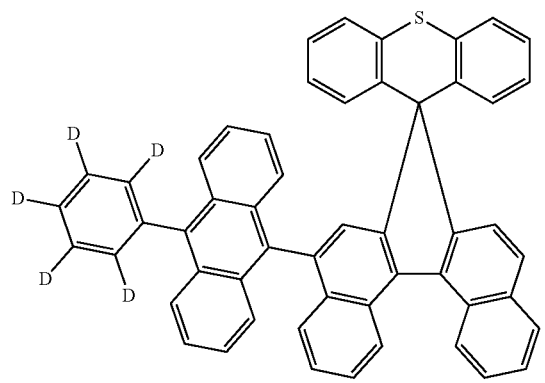

The present invention also provides an organic light emitting device including a first electrode, a second electrode opposite the first electrode, and an organic layer interposed between the first and second electrodes wherein the organic layer includes the compound represented by Formula I.

The organic layer including the organic light emitting compound of Formula I may include at least one layer selected from a hole injecting layer, a hole transport layer, a functional layer having functions of both hole injection and hole transport, a light emitting layer, an electron transport layer, and an electron injecting layer. The organic layer interposed between the first and second electrodes may include a light emitting layer. The light emitting layer may be composed of a host and a dopant. The organic light emitting compound of Formula I may be used as the host or dopant of the light emitting layer.

According to one embodiment of the present invention, the organic light emitting compound of Formula I may be used as the dopant. In this embodiment, the content of the organic light emitting compound of Formula I as the dopant in the light emitting layer is typically selected in the range of about 0.01 to about 20 parts by weight, based on 100 parts by weight the host.

The material for the electron transport layer functions to stably transport electrons injected from the electron injecting electrode (i.e. the cathode). The material for the electron transport layer may be any known electron transport material, and examples thereof include, but are not limited to, quinoline derivatives, particularly, tris(8-quinolinolate)aluminum (Alq3), TAZ, Balq, beryllium bis(benzoquinolin-10-olate (Bebq2), ADN, Compound 201, and Compound 202, and oxadiazole derivatives, such as PBD, BMD, and BND.

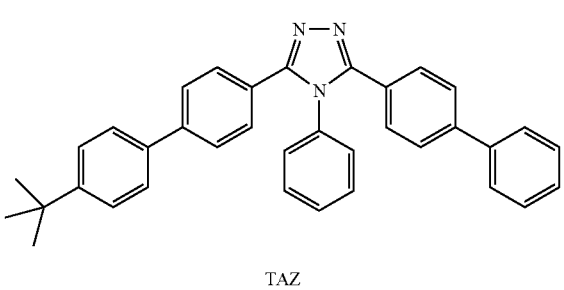

TAZ

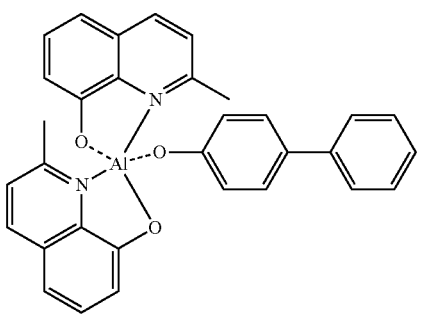

BAlq

Compound 201

Compound 202

BCP

PBD

BMD

BND

Hereinafter, the organic light emitting device of the present invention will be explained with reference to the FIGURE.

The FIGURE is a cross-sectional view schematically illustrating the structure of the organic light emitting device according to the present invention. The organic light emitting device of the present invention includes an anode 20, a hole transport layer 40, an organic light emitting layer 50, an electron transport layer 60, and a cathode 80. If necessary, the organic light emitting device may further include a hole injecting layer 30 and an electron injecting layer 70. In addition to these layers, one or more intermediate layers may be further formed in the organic light emitting device. A hole blocking layer or an electron blocking layer may be further formed in the organic light emitting device.

Referring to the FIGURE, a detailed description is given of a method for fabricating the organic light emitting device of the present invention.

First, an electrode material for the anode 20 is coated on a substrate 10 to form the anode 20. The substrate 10 may be any of those used in general organic electroluminescent (EL) devices. The substrate 10 is preferably an organic substrate or a transparent plastic substrate that is excellent in transparency, surface smoothness, ease of handling, and waterproofness. A highly transparent and conductive metal oxide, such as indium tin oxide (ITO), indium zinc oxide (IZO), tin oxide ($SnO_2$) or zinc oxide (ZnO), is used as the anode material.

A material for the hole injecting layer 20 is coated on the anode 20 by vacuum thermal evaporation or spin coating to form the hole injecting layer 30. Then, a material for the hole transport layer 40 is coated on the hole injecting layer 30 by vacuum thermal evaporation or spin coating to form the hole transport layer 40.

The material for the hole injecting layer is not specially limited so long as it is commonly used in the art. Example of such materials include 4,4',4"-tris(2-naphthyl(phenyl) amino)triphenylamine (2-TNATA), N,N'-di(1-naphthyl)-N, N'-diphenylbenzidine (NPD), N,N'-diphenyl-N,N'-bis(3-methylphenyl)-1,1'-biphenyl-4,4'-diamine (TPD), and N,N'-diphenyl-N,N'-bis[4-(phenyl-m-tolylamino)phenyl] biphenyl-4,4'-diamine (DNTPD).

The material for the hole transport layer is not specially limited so long as it is commonly used in the art. Example of such materials include N,N'-bis(3-methylphenyl)-N,N'-diphenyl-[1,1-biphenyl]-4,4'-diamine (TPD) and N,N'-di (naphthalen-1-yl)-N,N'-diphenylbenzidine (a-NPD).

Subsequently, the organic light emitting layer 50 is laminated on the hole transport layer 40. A hole blocking layer (not shown) may be optionally formed on the organic light emitting layer 50 by vacuum thermal evaporation or spin coating. The hole blocking layer blocks holes from entering the cathode through the organic light emitting layer. This role of the hole blocking layer prevents the life and efficiency of the device from deteriorating. A material having a very low highest occupied molecular orbital (HOMO) energy level is used for the hole blocking layer. The hole blocking material is not particularly limited so long as it has the ability to transport electrons and a higher ionization potential than the light emitting compound. Representative examples of suitable hole blocking materials include BAlq, BCP, and TPBI.

The electron transport layer 60 is deposited on the hole blocking layer by vacuum thermal evaporation or spin coating, and the electron injecting layer 70 is formed thereon. A metal for the cathode is deposited on the electron injecting layer 70 by vacuum thermal evaporation to form the cathode 80, completing the fabrication of the organic EL device. As the metal for the cathode, there may be used, for example, lithium (Li), magnesium (Mg), aluminum (Al), aluminum-lithium (Al—Li), calcium (Ca), magnesium-indium (Mg—In) or magnesium-silver (Mg—Ag). The organic EL device may be of top emission type. In this case, a transmissive material, such as ITO or IZO, may be used for the cathode.

One or more layers selected from the hole injecting layer, the hole transport layer, the electron blocking layer, the light emitting layer, the hole blocking layer, the electron transport layer, and the electron injecting layer may be formed by a monomolecular deposition or solution process. According to the monomolecular deposition process, the material for each layer is evaporated under heat and vacuum or reduced pressure to form the layer in the form of a thin film. According to the solution process, the material for each layer is mixed with a suitable solvent, and then the mixture is formed into a thin film by a suitable method, such as ink-jet printing, roll-to-roll coating, screen printing, spray coating, dip coating or spin coating.

The organic light emitting device of the present invention can be used in a variety of systems, such as flat panel displays, flexible displays, monochromatic flat panel lighting systems, white flat panel lighting systems, flexible monochromatic lighting systems, and flexible white lighting systems.

The present invention will be explained in more detail with reference to the following examples. However, it will be obvious to those skilled in the art that these examples are provided for illustrative purposes and are not intended to limit the scope of the invention.

Synthesis Example 1: Synthesis of Compound 1

[Reaction 1-1] Synthesis of Intermediate 1-a

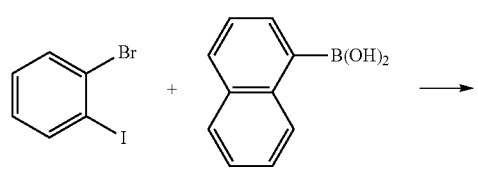

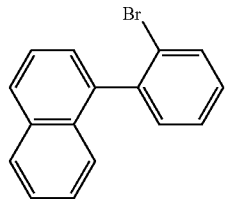

Intermediate 1-a

1-Naphthaleneboronic acid (12.5 g, 0.073 mol), 1-bromo-2-iodobenzene (17.3 g, 0.061 mol), tetrakis(triphenylphosphine)palladium (3.62 g, 0.003 mol), and potassium carbonate (16.9 g, 0.122 mol) were added to a mixed solvent of 150 mL of 1,4-dioxane, 150 mL of toluene, and 60 mL of distilled water. The mixture was refluxed for 12 h. The reaction mixture was allowed to cool to room temperature and extracted with ethyl acetate. Purification by column chromatography afforded 14.7 g (yield 85%) of Intermediate 1-a.

[Reaction 1-2] Synthesis of Intermediate 1-b

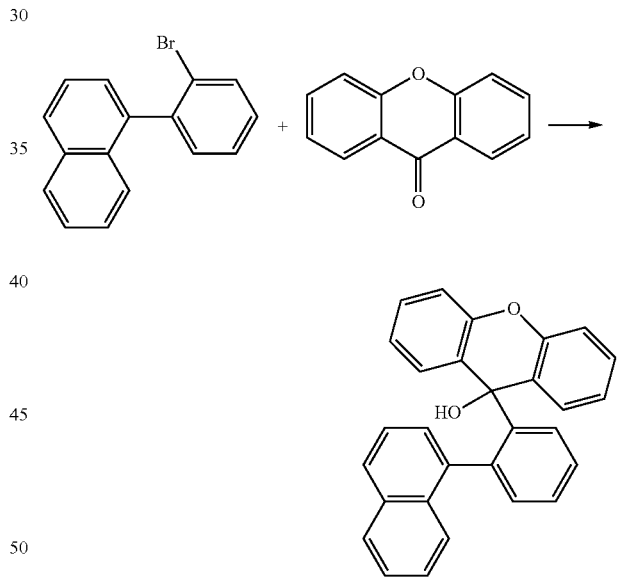

Intermediate 1-b

Intermediate 1-a (3.5 g, 12.2 mmol) was added to 50 mL of tetrahydrofuran and n-butyllithium (5.8 mL, 14.6 mmol) was added dropwise thereto at −78° C. The mixture was stirred for about 1 h. To the mixture was slowly added dropwise a solution of 9-xanthone (2.1 g, 10.8 mmol) in 10 mL of tetrahydrofuran at the same temperature. The resulting mixture was stirred for 2 h. Stirring was continued at room temperature for 12 h. The reaction mixture was extracted with ethyl acetate and recrystallized from diethyl ether, affording 3.2 g (yield 75%) of Intermediate 1-b.

[Reaction 1-3] Synthesis of Intermediate 1-c

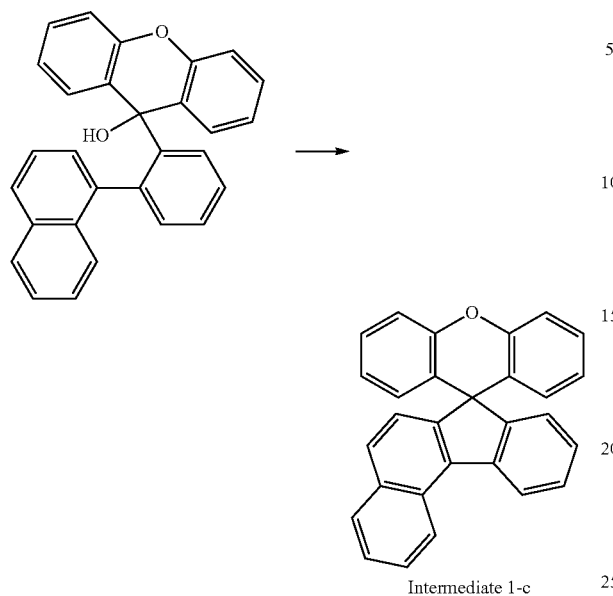

Intermediate 1-c

Intermediate 1-b (26.5 g, 66.3 mmol) was added to 300 mL of acetic acid. The mixture was heated to 80° C., and then 1-2 drops of an aqueous solution of hydrochloric acid was added thereto. The resulting mixture was refluxed for about 2 h. After cooling to room temperature, filtration of the reaction mixture afforded 22.8 g (yield 90%) of Intermediate 1-c.

[Reaction 1-4] Synthesis of Intermediate 1-d

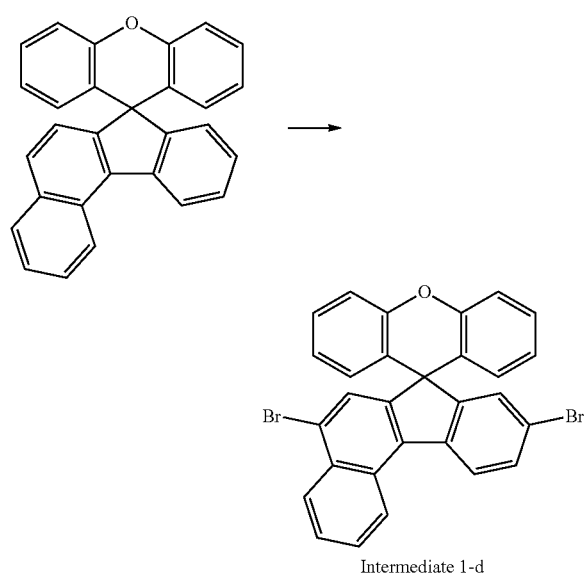

Intermediate 1-d

Intermediate 1-c (21 g, 0.055 mol) was added to 250 mL of dimethylformamide. The mixture was stirred at 0° C. To the mixture was added dropwise a solution of N-bromosuccinimide (21.5 g, 0.121 mol) in 70 mL of dimethylformamide. The resulting mixture was stirred for 6 h. The reaction mixture was precipitated in distilled water, filtered, and washed with hexane. The crude product was dissolved in dichloromethane, heated, treated with acid clay and activated carbon, washed with dichloromethane, and recrystallized from hexane, affording 17.8 g (yield 60%) of Intermediate 1-d.

[Reaction 1-5] Synthesis of Compound 1

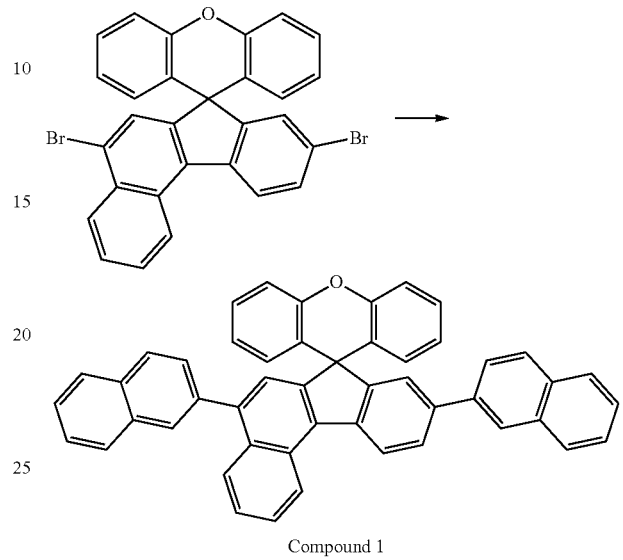

Compound 1

The procedure of Reaction 1-1 was repeated except that 2-naphthaleneboronic acid was used instead of 1-naphthaleneboronic acid and Intermediate 1-d synthesized in Reaction 1-4 was used instead of 1-bromo-2-iodobenzene. As a result, Compound 1 was prepared in a yield of 64%.

Synthesis Example 2: Synthesis of Compound 7

Compound 7 (yield 66%) was prepared in the same manner as in Synthesis Example 1, except that 9-phenanthreneboronic acid and 2-bromo-1-iodonaphthalene were used instead of 1-naphthaleneboronic acid and 1-bromo-2-iodobenzene in Reaction 1-1, respectively, and 1-naphthaleneboronic acid was used instead of 2-naphthaleneboronic acid in Reaction 1-5.

Synthesis Example 3: Synthesis of Compound 14

[Reaction 3-1] Synthesis of Intermediate 3-a
Intermediate 3-a (yield 88%) was prepared in the same manner as in Reactions 1-1 to 1-3, except that quinoline-5-boronic acid was used instead of 1-naphthaleneboronic acid and 2,4-dibromo-1-iodobenzene was used instead of 1-bromo-2-iodobenzene in Reaction 1-1.

[Reaction 3-2] Synthesis of Compound 14
The procedure of Reaction 1-1 was repeated except that 2-naphthaleneboronic acid was used instead of 1-naphthaleneboronic acid and Intermediate 3-a synthesized in Reaction 3-1 was used instead of 1-bromo-2-iodobenzene. As a result, Compound 14 was prepared in a yield of 70%.

Synthesis Example 4: Synthesis of Compound 19

Compound 19 (yield 62%) was prepared in the same manner as in Synthesis Example 1, except that 9-phenanthreneboronic acid was used instead of 1-naphthaleneboronic acid in Reaction 1-1, 10-thioxanthone was used instead of 9-xanthone in Reaction 1-2, and 1-naphthaleneboronic acid was used instead of 2-naphthaleneboronic acid in Reaction 1-5.

Synthesis Example 5: Synthesis of Compound 22

[Reaction 5-1] Synthesis of Intermediate 5-a

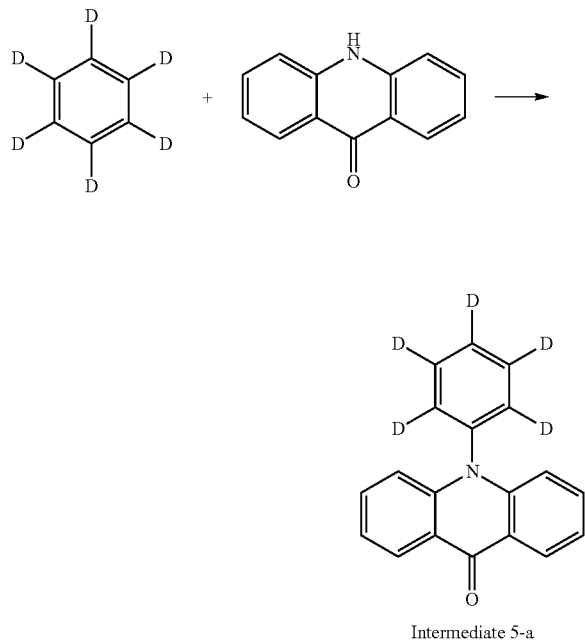

Intermediate 5-a

Pentadeuterochlorobenzene (11.7 g, 0.1 mol), 9-acridone (19.5 g, 0.1 mol), palladium acetate (0.08 g, 0.32 mmol), 2,2'-bis(diphenylphosphino)-1-1'-binaphthyl (0.26 g, 0.42 mmol), and sodium tert-butoxide (15.2 g, 0.16 mol) were added to 200 mL of toluene. The mixture was refluxed for 12 h. The reaction mixture was allowed to cool to room temperature, washed with methanol, and recrystallized from dichloromethane and methanol, affording 20.7 g (yield 75%) of Intermediate 5-a.

[Reaction 5-2] Synthesis of Compound 22

Compound 22 (yield 62%) was prepared in the same manner as in Synthesis Example 1, except that Intermediate 5-a synthesized in Reaction 5-1 was used instead of 9-xanthone in Reaction 1-2.

Synthesis Example 6: Synthesis of Compound 26

The procedure of Reaction 5-1 was repeated except that Intermediate 1-d synthesized in Reaction 1-4 was used instead of pentadeuterochlorobenzene and diphenylamine was used instead of 9-acridone. As a result, Compound 26 was prepared in a yield of 65%.

Synthesis Example 7: Synthesis of Compound 30

[Reaction 7-1] Synthesis of Intermediate 7-a

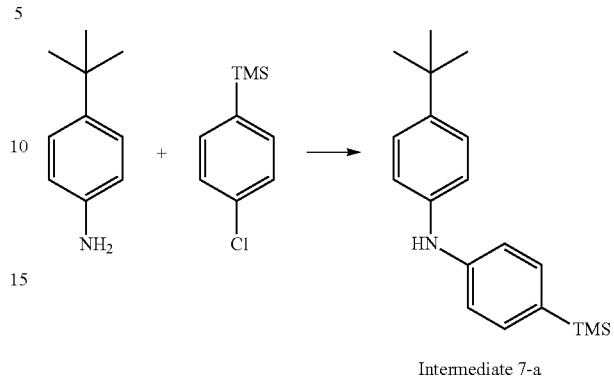

Intermediate 7-a

The procedure of Reaction 5-1 was repeated except that (4-chlorophenyl)trimethylsilane was used instead of pentadeuterochlorobenzene and 4-amino-tert-butylbenzene was used instead of 9-acridone. As a result, Intermediate 7-a was prepared in a yield of 75%.

[Reaction 7-2] Synthesis of Compound 30

The procedure of Reaction 5-1 was repeated except that Intermediate 1-d synthesized in Reaction 1-4 was used instead of pentadeuterochlorobenzene and Intermediate 7-a synthesized in Reaction 7-1 was used instead of 9-acridone. As a result, Compound 30 was prepared in a yield of 62%.

Synthesis Example 8: Synthesis of Compound 35

[Reaction 8-1] Synthesis of Intermediate 8-a

Intermediate 8-a (yield 58%) was prepared in the same manner as in Reactions 1-1 to 1-4, except that 10-thioxanthone was used instead of 9-xanthone in Reaction 1-2.

[Reaction 8-2] Synthesis of Intermediate 8-b

The procedure of Reaction 5-1 was repeated except that (4-chlorophenyl)trimethylsilane was used instead of pentadeuterochlorobenzene and 2-amino-5-methylpyridine was used instead of 9-acridone. As a result, Intermediate 8-b was prepared in a yield of 73%.

[Reaction 8-3] Synthesis of Compound 35

The procedure of Reaction 5-1 was repeated except that Intermediate 8-a synthesized in Reaction 8-1 was used instead of pentadeuterochlorobenzene and Intermediate 8-b synthesized in Reaction 8-2 was used instead of 9-acridone. As a result, Compound 35 was prepared in a yield of 64%.

Synthesis Example 9: Synthesis of Compound 38

[Reaction 9-1] Synthesis of Intermediate 9-a

The procedure of Reaction 5-1 was repeated except that 4-bromodibenzofuran was used instead of pentadeuterochlorobenzene and 1-amino-4-methylbenzene was used instead of 9-acridone. As a result, Intermediate 9-a was prepared in a yield of 72%.

[Reaction 9-2] Synthesis of Compound 38

The procedure of Reaction 5-1 was repeated except that Intermediate 1-d synthesized in Reaction 1-4 was used instead of pentadeuterochlorobenzene and Intermediate 9-a synthesized in Reaction 9-1 was used instead of 9-acridone. As a result, Compound 38 was prepared in a yield of 60%.

Synthesis Example 10: Synthesis of Compound 42

[Reaction 10-1] Synthesis of Intermediate 10-a

The procedure of Reaction 5-1 was repeated except that 4-chlorophenylboronic acid was used instead of pentadeuterochlorobenzene and diphenylamine was used instead of 9-acridone. As a result, Intermediate 10-a was prepared in a yield of 75%.

[Reaction 10-2] Synthesis of Compound 42

The procedure of Reaction 1-1 was repeated except that Intermediate 10-a synthesized in Reaction 10-1 was used instead of 1-naphthaleneboronic acid and Intermediate 8-a synthesized in Reaction 8-1 was used instead of 1-bromo-2-iodobenzene. As a result, Compound 42 was prepared in a yield of 65%.

Synthesis Example 11: Synthesis of Compound 44

[Reaction 11-1] Synthesis of Intermediate 11-a

The procedure of Reaction 5-1 was repeated except that chlorobenzene was used instead of pentadeuterochlorobenzene. As a result, Intermediate 11-a was prepared in a yield of 77%.

[Reaction 11-2] Synthesis of Intermediate 11-b

Intermediate 11-b (yield 58%) was prepared in the same manner as in Reactions 1-1 to 1-4, except that 9-phenanthreneboronic acid was used instead of 1-naphthaleneboronic acid in Reaction 1-1 and Intermediate 11-a synthesized in Reaction 11-1 was used instead of 9-xanthone in Reaction 1-2.

[Reaction 11-3] Synthesis of Intermediate 11-c

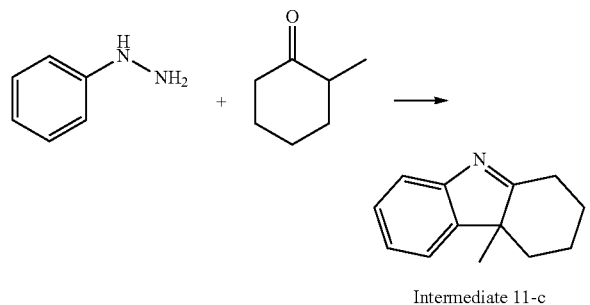

Intermediate 11-c

Phenylhydrazine (44.3 g, 0.41 mol) was added to 170 mL of acetic acid. The mixture was heated to 60° C. To the mixture was slowly added dropwise 2-methylcyclohexanone (45.9 g, 0.41 mol). The resulting mixture was refluxed for 8 h. After completion of the reaction, to the reaction mixture was added 100 mL of distilled water. The mixture was basified with sodium hydroxide and extracted with ethyl acetate. Purification by column chromatography afforded 63.8 g (yield 84%) of Intermediate 11-c.

[Reaction 11-4] Synthesis of Intermediate 11-d

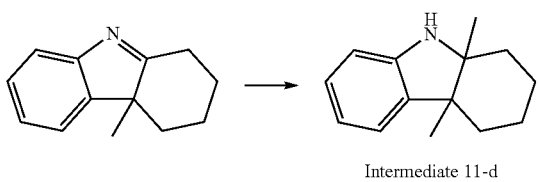

Intermediate 11-d

Intermediate 11-c (37 g, 0.2 mol) was dissolved in 400 mL of toluene. The solution was cooled to −10° C., and 188 mL of 1.6 M methyllithium was added dropwise thereto. After 3 h stirring, the reaction mixture was extracted with ethyl acetate. Purification by column chromatography afforded 30.6 g (yield 76%) of Intermediate 11-d.

[Reaction 11-5] Synthesis of Compound 44

The procedure of Reaction 5-1 was repeated except that Intermediate 11-b synthesized in Reaction 11-2 was used instead of pentadeuterochlorobenzene and Intermediate 11-d synthesized in Reaction 11-4 was used instead of 9-acridone. As a result, Compound 44 was prepared in a yield of 62%.

Synthesis Example 12: Synthesis of Compound 52

[Reaction 12-1] Synthesis of Intermediate 12-a

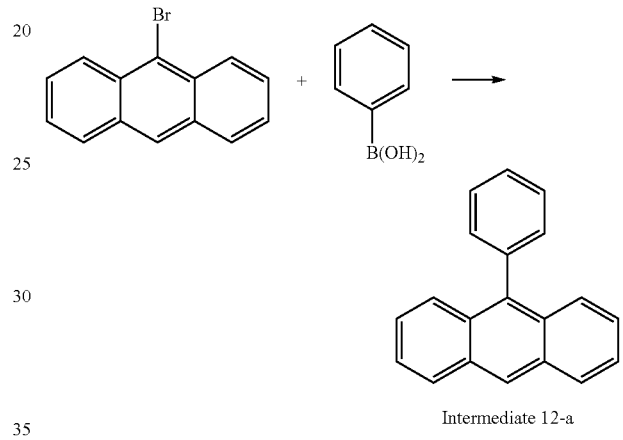

Intermediate 12-a

9-Bromoanthracene (15.0 g, 58 mmol), tetrakis(triphenylphosphine)palladium (2.02 g, 0.18 mmol), phenylboronic acid (8.5 g, 70 mol), and potassium carbonate (16.13 g, 116.7 mmol) were added to a reactor, and 75 mL of toluene, 75 mL of tetrahydrofuran, and 30 mL of water were added thereto. The temperature of the reactor was raised to 90° C. The mixture was stirred overnight. After completion of the reaction, the temperature of the reactor was reduced to room temperature. The reaction mixture was extracted with ethyl acetate. The extract was purified by column chromatography, affording 11.0 g (yield 74%) of Intermediate 12-a.

[Reaction 12-2] Synthesis of Intermediate 12-b

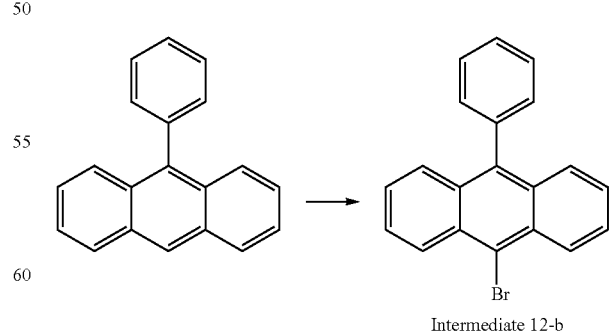

Intermediate 12-b

Intermediate 12-a (11.0 g, 43 mmol) was dissolved in 110 mL of N,N-dimethylformamide. To the solution was slowly added N-bromosuccinimide (8.5 g, 48 mmol). The mixture was stirred at room temperature. To the reaction solution was slowly added 100 mL of distilled water. The resulting mixture was stirred for about 1 h. The obtained solid was collected by filtration. The solid was sufficiently washed with distilled water and recrystallized from n-hexane, affording 12.0 g (yield 83%) of Intermediate 12-b.

[Reaction 12-3] Synthesis of Intermediate 12-c

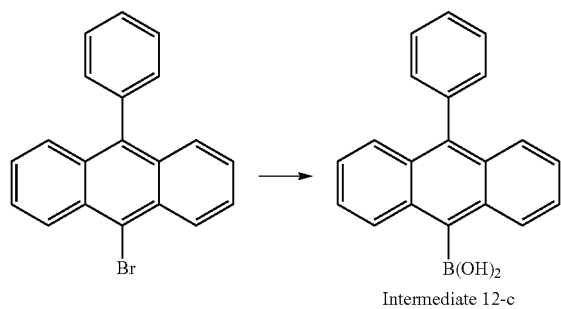 [SMILES: Brc1c2ccccc2c(-c2ccccc2)c2ccccc12 ; OB(O)c1c2ccccc2c(-c2ccccc2)c2ccccc12]

Intermediate 12-c

Intermediate 12-b (12.0 g, 36 mmol) was dissolved in 100 mL of tetrahydrofuran. After cooling to −78° C. under a nitrogen atmosphere, n-butyllithium (24.76 mL, 40 mmol) was slowly added dropwise for 30 min. The mixture was stirred at the same temperature for 1 h. To the mixture was added dropwise trimethyl borate (4.5 g, 43 mmol) at the same temperature. The resulting mixture was stirred at room temperature overnight. The reaction solution was acidified by dropwise addition of 2 N hydrochloric acid. After 1 h stirring, the mixture was extracted with ethyl acetate and recrystallized from hexane, affording 7.5 g (yield 69%) of Intermediate 12-c.

[Reaction 12-4] Synthesis of Intermediate 12-d

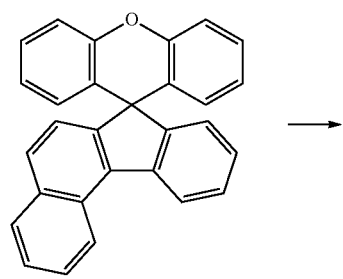

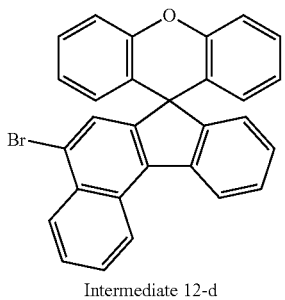

Intermediate 12-d

The procedure of Reaction 12-2 was repeated except that Intermediate 1-c was used instead of Intermediate 12-a. As a result, Intermediate 12-d was prepared in a yield of 50%.

[Reaction 12-5] Synthesis of Compound 52

The procedure of Reaction 1-1 was repeated except that Intermediate 12-c synthesized in Reaction 12-3 was used instead of 1-naphthaleneboronic acid and Intermediate 12-d synthesized in Reaction 12-4 was used instead of 1-bromo-2-iodobenzene. As a result, Compound 52 was prepared in a yield of 52%.

Synthesis Example 13: Synthesis of Compound 53

[Reaction 13-1] Synthesis of Intermediate 13-a

Intermediate 13-a (yield 89%) was prepared in the same manner as in Reactions 1-1 to 1-3, except that 9-phenanthreneboronic acid was used instead of 1-naphthaleneboronic acid in Reaction 1-1.

[Reaction 13-2] Synthesis of Compound 53

Compound 53 (yield 50%) was prepared in the same manner as in Synthesis Example 12, except that Intermediate 13-a synthesized in Reaction 13-1 was used instead of Intermediate 1-c in Reaction 12-4.

Examples 1-11: Fabrication of Organic Light Emitting Diodes

ITO glass was patterned to have a light emitting area of 2 mm×2 mm, followed by cleaning. After the cleaned ITO glass was mounted in a vacuum chamber, the base pressure was adjusted to $1\times10^{-6}$ torr. DNTPD (700 Å), α-NPD (300 Å), BH1 as a host, and 3 wt % of each of the compounds prepared in Synthesis Examples 1-11 as a dopant were sequentially co-deposited on the ITO to form a light emitting layer. Thereafter, an $Alq_3$ layer (350 Å), a LiF layer (5 Å), and an Al layer (1,000 Å) were formed in this order on the light emitting layer to fabricate an organic light emitting diode. The luminescent properties of the organic light emitting diode were measured at 0.4 mA.

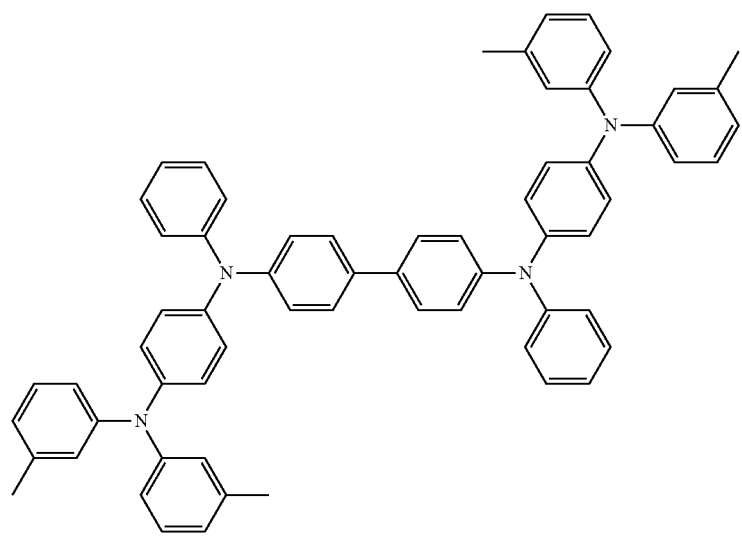
[DNTPD]
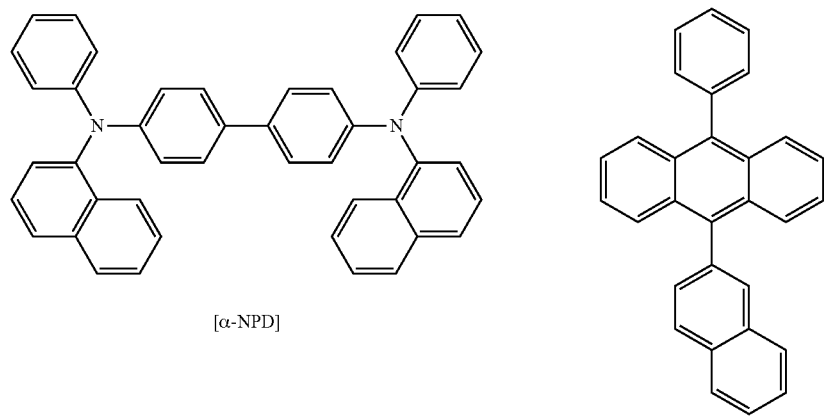
[α-NPD]
[BH1]
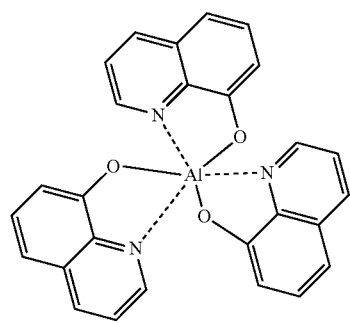
[Alq₃]
Comparative Examples 1-2
Organic light emitting devices were fabricated in the same manner as in Examples 1-11, except that Compound 101 (Comparative Example 1) and Compound 102 (Comparative Example 2) were used as dopants instead of the compounds prepared in Synthesis Examples 1-11.

Compound 101

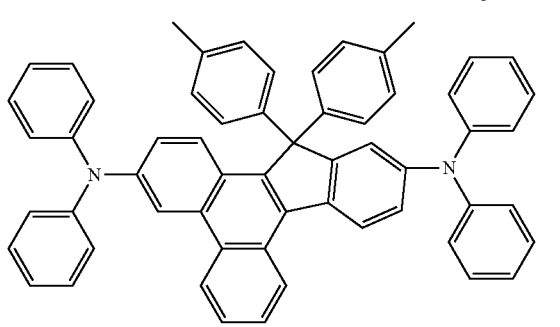

Compound 102

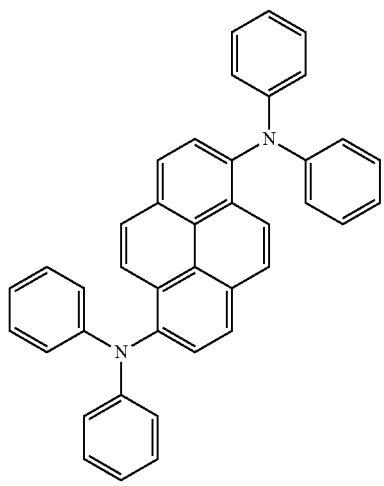

Examples 12-13: Fabrication of Organic Light Emitting Diodes

ITO glass was patterned to have a light emitting area of 2 mm×2 mm, followed by cleaning. After the cleaned ITO glass was mounted in a vacuum chamber, the base pressure was adjusted to $1×10^{-6}$ torr. A DNTPD layer (700 Å) and an α-NPD layer (300 Å) were sequentially formed on the ITO glass, and a mixture of each of Compounds 52 and 53 as a host and BD1 (3%) as a dopant was deposited to a thickness of 250 Å thereon to form a light emitting layer. Thereafter, an $Alq_3$ layer (350 Å), a LiF layer (5 Å), and an Al layer (1,000 Å) were formed in this order on the light emitting layer to fabricate an organic light emitting device. The luminescent properties of the organic light emitting device were measured at 0.4 mA. The structure of BD1 is as follows:

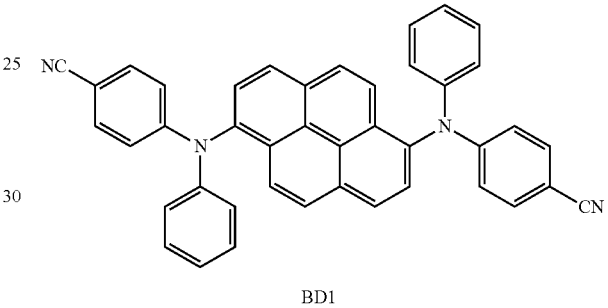

BD1

Comparative Examples 3-4

Organic light emitting devices were fabricated in the same manner as in Example 12, except that Compounds 103 (Comparative Example 3) and 104 (Comparative Example 4) were used as instead of Compound 52. The structures of Compounds 103 and 140 are as follows:

The organic light emitting devices fabricated in Examples 1-11 and Comparative Examples 1-2 were measured for voltage, luminance, quantum efficiency, and color coordinates. The results are shown in Table 1.

TABLE 1

| Example No. | Host | Dopant | Voltage (V) | Luminance (Cd/m²) | Quantum efficiency | CIE x | CIE y |
|---|---|---|---|---|---|---|---|
| Example 1 | BH1 | Compound 1 | 3.8 | 770 | 8.2 | 0.14 | 0.11 |
| Example 2 | BH1 | Compound 7 | 3.9 | 771 | 8.0 | 0.14 | 0.11 |
| Example 3 | BH1 | Compound 14 | 3.8 | 785 | 7.9 | 0.14 | 0.12 |
| Example 4 | BH1 | Compound 19 | 3.8 | 784 | 8.1 | 0.14 | 0.11 |
| Example 5 | BH1 | Compound 22 | 3.8 | 780 | 8.1 | 0.14 | 0.11 |
| Example 6 | BH1 | Compound 26 | 3.8 | 769 | 8.0 | 0.14 | 0.12 |
| Example 7 | BH1 | Compound 30 | 3.8 | 762 | 8.2 | 0.14 | 0.11 |
| Example 8 | BH1 | Compound 35 | 3.8 | 772 | 8.3 | 0.14 | 0.11 |
| Example 9 | BH1 | Compound 38 | 3.8 | 798 | 7.9 | 0.14 | 0.11 |
| Example 10 | BH1 | Compound 42 | 3.8 | 769 | 7.9 | 0.14 | 0.11 |
| Example 11 | BH1 | Compound 44 | 3.9 | 777 | 8.1 | 0.14 | 0.11 |
| Comparative Example 1 | BH1 | Compound 101 | 3.7 | 750 | 6.0 | 0.14 | 0.13 |
| Comparative Example 2 | BH1 | Compound 102 | 4.3 | 515 | 5.1 | 0.15 | 0.17 |

Compound 103

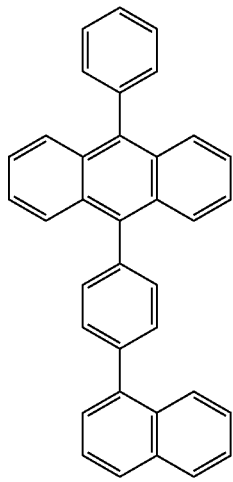

Compound 104

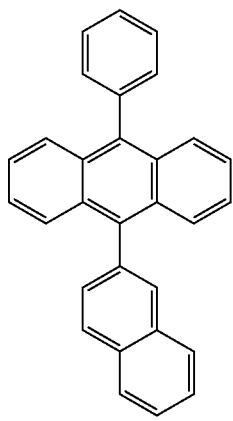

The organic light emitting devices fabricated in Examples 12-13 and Comparative Examples 3-4 were measured for voltage, luminance, quantum efficiency, and color coordinates. The results are shown in Table 2.

TABLE 2

| Example No. | Host | Dopant | Voltage (V) | Luminance (Cd/m²) | Quantum efficiency | CIE x | CIE y |
| --- | --- | --- | --- | --- | --- | --- | --- |
| Example 12 | Compound 52 | BD1 | 3.8 | 759 | 8.2 | 0.14 | 0.12 |
| Example 13 | Compound 53 | BD1 | 3.8 | 765 | 8.0 | 0.14 | 0.11 |
| Comparative Example 3 | Compound 103 | BD1 | 4.3 | 550 | 5.5 | 0.14 | 0.12 |
| Comparative Example 4 | Compound 104 | BD1 | 4.3 | 520 | 5.1 | 0.14 | 0.12 |

As can be seen from the results in Tables 1 and 2, the organic light emitting devices of Examples 1-13, which were fabricated using the novel inventive compounds, were driven at low voltages and showed high luminance and efficiency values compared to those of Comparative Examples 1-4.

What is claimed is:

1. An organic light emitting compound represented by Formula I:

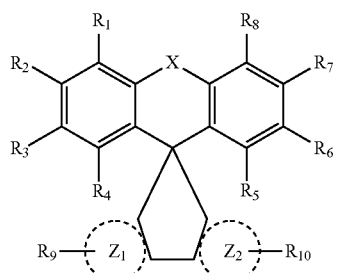

(I)

wherein:

X is O, S or $SiR_{12}R_{13}$, $R_1$ to $R_8$ are identical to or different from each other and are each independently selected from hydrogen, substituted or unsubstituted $C_1$-$C_{10}$ alkyl groups, and substituted or unsubstituted $C_6$-$C_{20}$ aryl groups, $R_9$ to $R_{10}$ are identical to or different from each other and are each independently selected from substituted or unsubstituted $C_6$-$C_{30}$ aryl groups, substituted or unsubstituted $C_6$-$C_{30}$ arylamine groups, and substituted or unsubstituted $C_2$-$C_{30}$ heteroaryl groups having one or more heteroatoms selected from O, N, S, and P, $R_{12}$ to $R_{13}$ are identical to or different from each other and are each independently selected from substituted or unsubstituted $C_6$-$C_{20}$ aryl groups, and

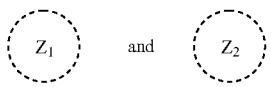

in Formula I are different from and are each independently selected from the following structures C3 to C9:

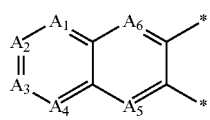

C3

-continued

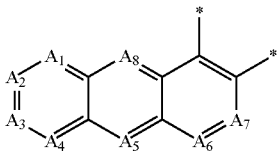
C4

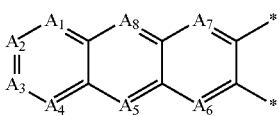
C5

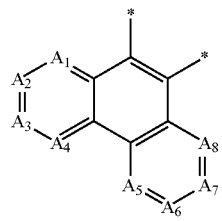
C6

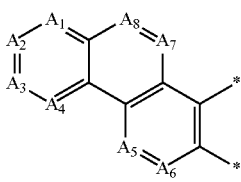
C7

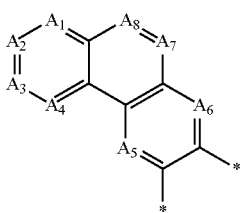
C8

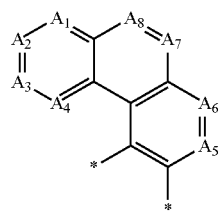
C9 wherein A1 to A10 are identical to or different from each other and are each independently N or CR, wherein R is hydrogen, and * indicates a site at which the structure is bonded to Formula I.

2. An organic light emitting compound represented by Formula I:

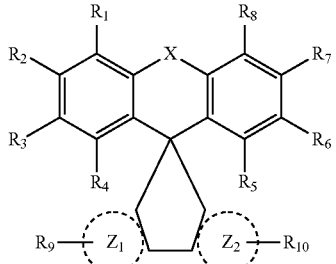
(I)

wherein:

X is O, S or $SiR_{12}R_{13}$, $R_1$ to $R_8$ are identical to or different from each other and are each independently selected from hydrogen, substituted or unsubstituted $C_1$-$C_{10}$ alkyl groups, and substituted or unsubstituted $C_6$-$C_{20}$ aryl groups, and at least one of $R_1$ to $R_8$ is not hydrogen, $R_9$ to $R_{10}$ are identical to or different from each other and are each independently selected from substituted or unsubstituted $C_6$-$C_{30}$ aryl groups, $R_{12}$ to $R_{13}$ are identical to or different from each other and are each independently selected from substituted or unsubstituted $C_6$-$C_{20}$ aryl groups, and

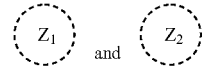

in Formula I are identical or different from each other and are each independently selected from the following structures C2 to C9:

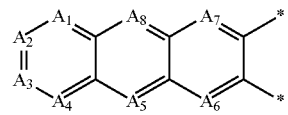
C5

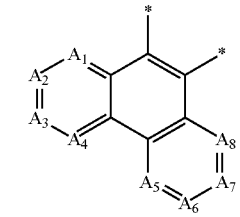
C6

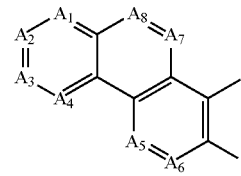
C7

-continued

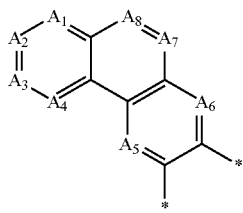
C8

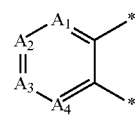
C1

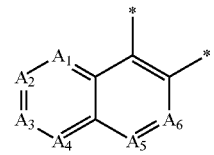
C2

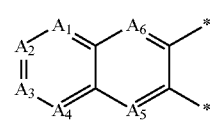
C3

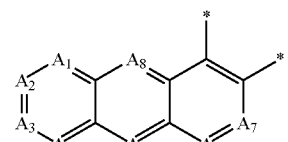
C4

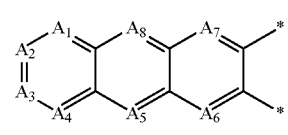
C5

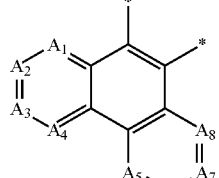
C6

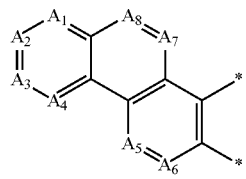
C7

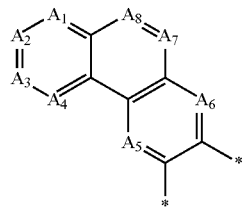
C8

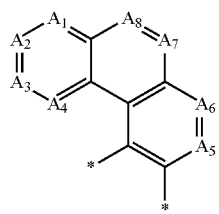
C9 wherein A1 to A10 are identical to or different from each other and are each independently N or CR, wherein R is hydrogen, and * indicates a site at which the structure is bonded to Formula I.

3. An organic light emitting compound represented by Formula I:

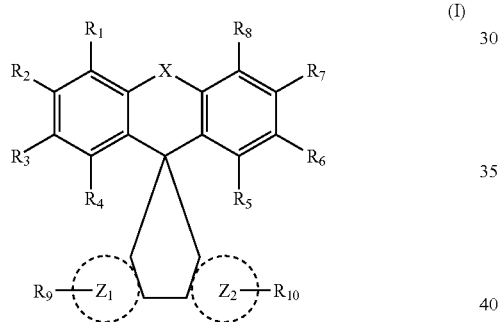
(I)

wherein:

X is S or $SiR_{12}R_{13}$, $R_1$ to $R_8$ are identical to or different from each other and are each independently selected from hydrogen, substituted or unsubstituted $C_1$-$C_{10}$ alkyl groups, and substituted or unsubstituted $C_6$-$C_{20}$ aryl groups, $R_9$ to $R_{10}$ are identical to or different from each other and are each independently selected from substituted or unsubstituted $C_6$-$C_{30}$ aryl groups, substituted or unsubstituted $C_6$-$C_{30}$ arylamine groups, and substituted or unsubstituted $C_2$-$C_{30}$ heteroaryl groups having one or more heteroatoms selected from O, N, S, and P, $R_{12}$ to $R_{13}$ are identical to or different from each other and are each independently selected from substituted or unsubstituted $C_6$-$C_{20}$ aryl groups, and

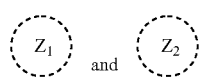

in Formula I are identical or different from each other and are each independently selected from the following structures C1 to C9:

wherein A1 to A10 are identical to or different from each other and are each independently N or CR, wherein R is hydrogen, and * indicates a site at which the structure is bonded to Formula I, wherein at least one of (Z₁) and (Z₂); is not C1.
4. The organic light emitting compound according to claim 3, wherein the compound of Formula I is selected from the following compounds 17, 18, 20, 35, 42, 59 and 60:
Compound 17
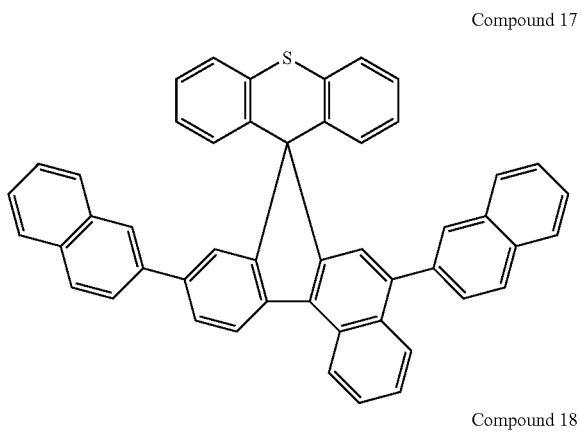
Compound 18
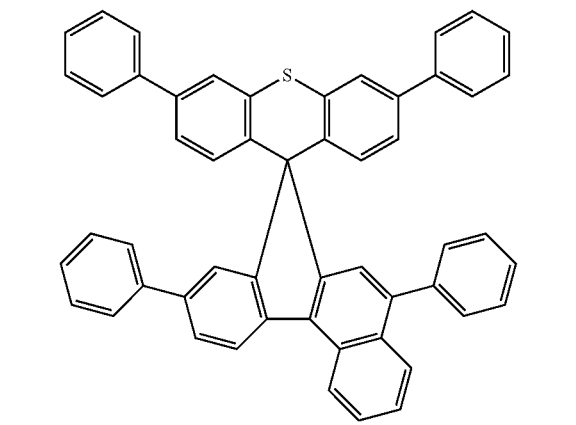
Compound 20
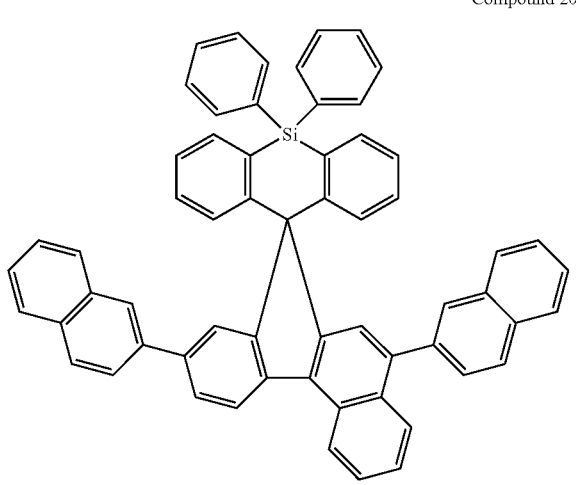
Compound 35
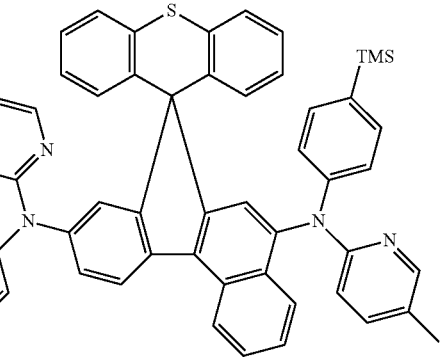
Compound 42
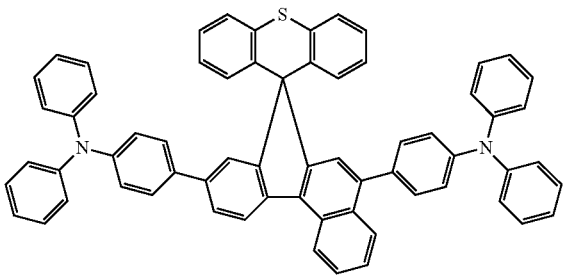
Compound 59
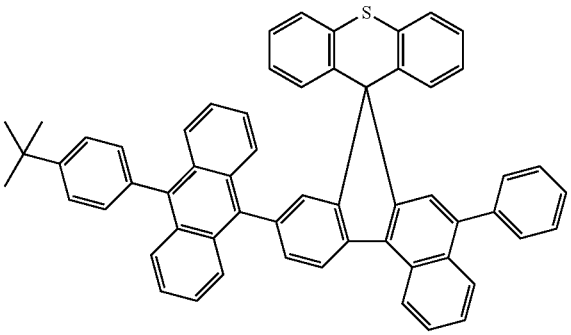
Compound 60
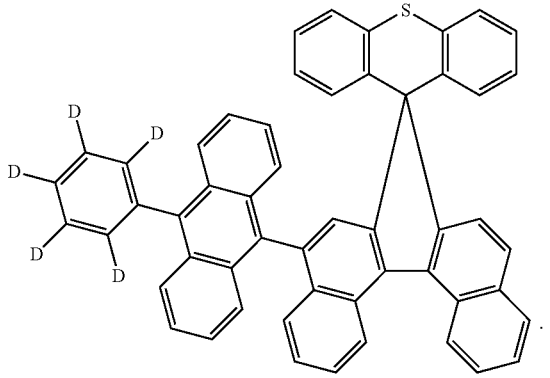
* * * * *